(12) United States Patent
Tabuchi et al.

(10) Patent No.: US 8,741,601 B2
(45) Date of Patent: Jun. 3, 2014

(54) METHOD FOR PRODUCING A CELL CAPABLE OF HIGH-YIELD PRODUCTION OF HETEROPROTEINS

(75) Inventors: Hisahiro Tabuchi, Tokyo (JP); Tomoya Sugiyama, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/138,909

(22) PCT Filed: Apr. 21, 2010

(86) PCT No.: PCT/JP2010/057030
§ 371 (c)(1),
(2), (4) Date: Oct. 21, 2011

(87) PCT Pub. No.: WO2010/123014
PCT Pub. Date: Oct. 28, 2010

(65) Prior Publication Data
US 2012/0045795 A1   Feb. 23, 2012

(30) Foreign Application Priority Data
Apr. 22, 2009   (JP) ................ 2009-103596

(51) Int. Cl.
| | | |
|---|---|---|
| C12P 21/06 | (2006.01) | |
| C12N 15/82 | (2006.01) | |
| C12N 15/74 | (2006.01) | |
| C12N 1/19 | (2006.01) | |
| C12N 5/02 | (2006.01) | |

(52) U.S. Cl.
USPC .......... 435/69.6; 435/455; 435/468; 435/471; 435/325; 435/352

(58) Field of Classification Search
None
See application file for complete search history.

(56) References Cited

U.S. PATENT DOCUMENTS

| | | |
|---|---|---|
| 5,658,786 A | 8/1997 | Smith et al. |
| 6,184,007 B1 | 2/2001 | Dusch et al. |
| 6,225,115 B1 | 5/2001 | Smith et al. |
| 6,251,613 B1 | 6/2001 | Kishimoto et al. |
| 6,316,238 B1 | 11/2001 | Nakamura et al. |
| 6,812,339 B1 | 11/2004 | Venter et al. |
| 7,413,536 B1 | 8/2008 | Dower et al. |
| 7,919,086 B2 | 4/2011 | Nakano et al. |
| 2003/0165495 A1 | 9/2003 | Carulli et al. |
| 2005/0221466 A1 | 10/2005 | Liao et al. |
| 2005/0265983 A1 | 12/2005 | Melamed et al. |
| 2006/0014937 A1 | 1/2006 | Kang et al. |
| 2007/0162995 A1 | 7/2007 | Good et al. |
| 2007/0166362 A1 | 7/2007 | Sakuma et al. |
| 2007/0190599 A1 | 8/2007 | Nakano et al. |
| 2009/0191591 A1 | 7/2009 | Tabuchi et al. |
| 2009/0221442 A1 | 9/2009 | Dower et al. |
| 2010/0167346 A1 | 7/2010 | Tabuchi et al. |
| 2010/0233759 A1 | 9/2010 | Tabuchi et al. |
| 2010/0248359 A1 | 9/2010 | Nakano et al. |
| 2011/0003334 A1 | 1/2011 | Tabuchi et al. |
| 2011/0014654 A1 | 1/2011 | Tabuchi et al. |

FOREIGN PATENT DOCUMENTS

| | | |
|---|---|---|
| CN | 1612689 A | 5/2005 |
| CN | 1838969 A | 9/2006 |
| EP | 1 212 619 B1 | 5/2007 |
| EP | 2 213 746 A1 | 8/2010 |
| JP | 08-191693 A | 7/1996 |
| JP | 10-075787 A | 3/1998 |
| JP | 10-191984 A | 7/1998 |
| JP | 2000-228990 A | 8/2000 |
| JP | 2005-525100 A | 8/2005 |
| JP | 2006-506086 A | 2/2006 |
| WO | WO-92/04381 A1 | 3/1992 |
| WO | WO-97/27485 A1 | 7/1997 |
| WO | WO-01/20331 A1 | 3/2001 |
| WO | WO-02/092768 A2 | 11/2002 |
| WO | WO-03/039485 A2 | 5/2003 |
| WO | WO-2005/076015 A1 | 8/2005 |
| WO | WO-2006/006693 A1 | 1/2006 |
| WO | WO-2006/119115 A2 | 11/2006 |
| WO | WO-2007/056507 A1 | 5/2007 |
| WO | WO-2007/119774 A1 | 10/2007 |
| WO | WO 2008/114673 A1 | 9/2008 |
| WO | WO 2009/020144 A1 | 2/2009 |
| WO | WO 2009/051109 A1 | 4/2009 |
| WO | WO 2009/054433 A1 | 4/2009 |

OTHER PUBLICATIONS

U.S. Appl. No. 13/368,945, filed Feb. 8, 2012, Tabuchi et al.
Alper, Seth L., "Molecular physiology of SLC4 anion exchangers," Exp. Physiol., 2006, 91:153-161.
Arden et al., "Life and death in mammalian cell culture: strategies for apoptosis inhibition," Trends in Biotechnology, Apr. 2004, 22(4):174-180.
Bell et al., "Genetic Engineering of Hybridoma Glutamine Metabolism," Enzyme and Microbial Technology, 1995, 17(2):98-106.

(Continued)

Primary Examiner — Kagnew H Gebreyesus
(74) Attorney, Agent, or Firm — Foley & Lardner LLP

(57) ABSTRACT

The present invention provides a cell capable of high-yield production of polypeptides and a method for producing the same.

The present invention relates to a method for producing a cell capable of high-yield production of a desired polypeptide, wherein a strongly bicarbonate transporter-expressing cell into which DNA encoding the desired polypeptide has been introduced is cultured in the presence of a high concentration of methotrexate and a cell capable of high-yield production of the desired polypeptide is selected from among surviving cells.

16 Claims, 6 Drawing Sheets

(56) References Cited

OTHER PUBLICATIONS

Butler, Michael, "Animal cell cultures: recent achievements and perspectives in the production of biopharmaceuticals," Appl. Microbiol. Biotechnol., Aug. 2005, 68(3):283-291.

Chambard et al., "Sugar transport by mammalian members of the SLC26 superfamily of anion-bicarbonate exchangers," J. Physiol., 2003, 550:667-677.

Christensen et al., "High expression of the taurine transporter TauT in primary cilic of NIH3T3 fibroblasts," Cell Biology International, 2005, 29:347-351.

Christie et al., "The Adaptation of BHK Cells to a Non-Ammoniagenic Glutamate-Based Culture Medium," Biotechnology and Bioengineering, Aug. 5, 1999, 64(3):298-309.

Database DDBJ/EMBL/GenBank [online], Accession No. NM_000342, uploaded Sep. 25, 2007, Keskanokwong et al., Definition: Homo sapiens solute carrier family 4, anion exchanger, member 1 (erythrocyte membrane protein band 3, Diego blood group) (SLC4A1), mRNA, retrieved Nov. 11, 2008, 12 pages.

Database EMBL [Online] Jul. 23, 1992, XP002593029, retrieved from EBI accession No. EMBL:M95495, 3 pages.

Database Uniprot [Online] Jan. 10, 2006, XP002593032, retrieved from EBI accession No. UNIPROT:Q2VRP7, 1 page.

Database UniProt [Online] Jul. 1, 1993, XP002593028, retrieved from EBI accession No. UNIPROT:Q00589, 2 pages.

Database UniProt [Online] Jun. 1, 2001, "RecName: Full=Cysteine sulfinic acid decarboxylase; EC=4.1.1.29; AltName: Full=Cysteine-sulfinate decarboxylase; AltName: Full=Sulfinoalanine decarboxylase;" XP002597738 retrieved from EBI accession No. UNIPROT:Q9DBE0 Database accession No. Q9DBE0, 2 pages.

Database Uniprot [Online] Mar. 15, 2005, XP002593030, retrieved from EBI accession No. UNIPROT:Q5F431, 1 page.

Database Uniprot [Online] Oct. 1, 2000, XP002593031, retrieved from EBI accession No. UNIPROT:Q9MZ34, 2 pages.

de la Cruz Edmonds et al., "Development of Transfection and High-Producer Screening Protocols for the CHOK1SV Cell System," Molecular Biology, Oct. 1, 2006, 34(2):179-190.

de la Rosa et al., "Evidence for a Rate-Limiting Role of Cysteinesulfinate Decarboxylase Activity in Taurine Biosynthesis In Vivo," Comp. Biochem. Physiol., 1985, 81B(3):565-571.

Dusch et al., "Expression of the *Corynebacterium glutamicum* panD Gene Encoding L-Aspartate-alpha-Decarboxylase Leads to Pantothenate Overproduction in *Escherichia coli*," Applied and Environmental Microbiology, Apr. 1999, 65(4):1530-1539.

Final Office Action dated Dec. 17, 2010 in U.S. Appl. No. 12/226,195.

Final Office Action dated Mar. 1, 2012 in U.S. Appl. No. 12/733,052.

Final Office Action dated Mar. 2, 2012 in U.S. Appl. No. 12/734,283.

Final Office Action dated Aug. 23, 2011 in U.S. Appl. No. 12/733,815.

Ganapathy et al., "Expression and Regulation of the Taurine Transporter in Cultured Cell Lines of Human Origin," Advances in Experimental Medicine and Biology, 1994, 359:51-57, XP009123192.

GenBank Accession No. AEQ38544, Oct. 2011, 2 pages.

GenBank Accession No. EGW01898, Aug. 2011, 2 pages.

Good et al., "Engineering nitrogen use efficiency with alanine aminotransferase," Canadian Journal of Botany, Mar. 1, 2007, 85(3):252-262.

Griffith, Owen W., "Crysteinesulfinate Metabolism, Altered Partitioning Between Transamination and Decarboxylation Following Administration of β-Methyleneaspartate," J. Biol. Chem., Feb. 10, 1983, 258(3):1591-1598.

Hammer et al., "β-Alanine but not taurine can function as an organic osmolyte in preimplantation mouse embryos cultured from fertilized eggs," Molecular Reproduction and Development, Oct. 2003, 66(2):153-161.

Han et al., "Is TauT an Anti-Apoptotic Gene?" Taurine 6, Oja et al. Eds., 2006, 59-67.

Hwang et al., "Expression and purification of recombinant human angiopoietin-2 produced in Chinese hamster ovary cells," Protein Expression and Purification, 2005, 39:175-183.

Ifandi et al., "Regulation of Cell Proliferation and Apoptosis in CHO-K1 Cells by the Coexpression of c-Myc and Bcl-2," Biotechnol. Prog., 2005, 21:671-677.

Ito et al., "Expression of taurine transporter is regulated through the TonE (tonicity-responsive element)/TonEBP (TonE-binding protein) pathway and contributes to cytoprotection in HepG2 cells," Biochem. J., 2004, 382:177-182.

Jhiang et al., "Cloning of the human taurine transporter and characterization of taurine uptake in thyroid cells," FEBS Letters, Mar. 1993, 318(2):139-144.

Kalwy et al., "Toward More Efficient Protein Expression," Molecular Biotechnology, Oct. 2006, 34(2):151-156.

Kennell et al,. "Principles and Practices of Nucleic Acid Hybridization," Prog. Nucleic Acid Res. Mol. Biol., 1971, 11:259-270.

Kim et al., "Response of recombinant Chinese hamster ovary cells to hyperosmotic pressure: effect of Bcl-2 overexpression," Journal of Biotechnology, 2002, 95:237-248.

Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.

Kondo et al., "Modulation of apoptosis by endogenous Bcl-xL expression in MKN-45 human gastric cancer cells," Oncogene, 1998, 17:2585-2591.

Lee et al., "Development of Apoptosis-Resistant Dihydrofolate Reductase-Deficient Chinese Hamster Ovary Cell Line," Biotechnol. Bioengineer., 2003, 82:872-876.

Liu et al., "Cloning and expression of a cDNA encoding the transporter of taurine and β-alanine in mouse brain," Proc. Natl. Acad. Sci. USA, Dec. 1992, 89(24):12145-12149.

Lux et al., "Cloning and characterization of band 3, the human erythrocyte anion-exchange protein (AE1)," Proc. Natl. Acad. Sci. USA, Dec. 1989, 86:9089-9093.

Miyasaka et al., "Characterization of Human Taurine Transporter Expressed in Insect Cells Using a Recombinant *Baculovirus*," Protein Expression and Purification, 2001, 23(3):389-397.

Morgan et al., "Interactions of transmembrane carbonic anhydrase, CAIX, with bicarbonate transporters," Am. J. Physiol. Cell Physiol., Aug. 2007, 293(2):C738-C748.

Ngo et al., "Computational Complexity, Protein Structure Prediction, and the Levinthal Paradox," The Protein Folding Problem and Tertiary Structure Prediction, Merz et al. (Eds.), 1994, 433 and 492-495.

Office Action dated Jan. 6, 2011 in U.S. Appl. No. 12/733,815.

Office Action dated May 12, 2011 in U.S. Appl. No. 12/733,052.

Office Action dated May 18, 2010 in U.S. Appl. No. 12/226,195.

Office Action dated Aug. 3, 2011 in U.S. Appl. No. 12/734,283.

Office Action dated Aug. 9, 2011 in U.S. Appl. No. 12/450,161.

Porter et al., "Non-steady-state kinetics of brain glutamate decarboxylase resulting from interconversion of the apo- and holoenzyme," Biochimica et Biophysica Acta, 1988, 874:235-244.

Ramamoorthy et al., "Functional characterization and chromosomal localization of a cloned taurine transporter from human placenta," Biochem. J., 1994, 300:893-900.

Reymond et al., "Molecular cloning and sequence analysis of the cDNA encoding rat liver cysteine sulfinate decarboxylase (CSD)," Biochimica et Biophysica Acta, 1996, 1307:152-156.

Rudinger, J., "Characteristics of the amino acids as components of a peptide hormone sequence," Peptide Hormones, Parsons (Ed.), 1976, 1-7.

Shen et al., "Expression of Anion Exchanger 1 Sequestrates p16 in the Cytoplasm in Gastric and Colonic Adenocarcinoma," Neoplasia, Oct. 2007, 9(10):812-819.

Smith et al., "Cloning and Expression of a High Affinity Taurine Transporter from Rat Brain," Molecular Pharmacology, 1992, 42(4):563-569.

Tabuchi et al., "Overexpression of Taurine Transporter in Chinese Hamster Ovary cells Can Enhance Cell Viability and Product Yield, While Promoting Glutamine Consumption," Biotechnology and Bioengineering, 2010, 107(6):998-1003.

(56) References Cited

OTHER PUBLICATIONS

Tang et al., "Protein Phosphorylation and Taurine Biosynthesis In Vivo and In Vitro," Journal of Neuroscience, Sep. 15, 1997, 17(18):6947-6951.

Tappaz et al., "Characterization of the cDNA Coding for Rat Brain Cysteine Sulfinate Decarboxylase: Brain and Liver Enzymes are Identical Proteins Encoded by Two Distince mRNAs," J. Neurochem., 1999, 73(3):903-912.

Tinland et al., "*Agrobacterium tumefaciens* transfers single-stranded transferred DNA (T-DNA) into the plant cell nucleus," Proc. Natl. Acad. Sci. USA, Aug. 1994, 91:8000-8004.

Trill et al., "Production of monoclonal antibodies in COS and CHO cells," Current Opinion in Biotechnology, 1995, 6:553-560.

Uchida et al., "Molecular cloning of the cDNA for an MDCK cell Na+- and Cl⁻dependent taurine transporter that is regulated by hypertonicity," PNAS, Sep. 1992, 89(17):8230-8234.

Voss et al., "Regulation of the expression and subcellular localization of the taurine transporter TauT in mouse NIH3T3 fibroblasts," Eur. J. Biochem., Dec. 2004, 271(23-24):4646-4658.

Wirth et al., "Isolation of overproducing recombinant mammalian cell lines by a fast and simple selection procedure," Gene, 1988, 73:419-426.

Wu et al., "Overexpression of Anion Exchanger 2 in Human Hepatocellular Carcinoma," Chinese Journal of Physiology, 2006, 49(4):192-198.

Yang et al., "Human Hepatitis B Viral e Antigen Interacts with Cellular Interleukin-1 Receptor Accessory Protein and Triggers Interleukin-1 Response," Journal of Biological Chemistry, Nov. 10, 2006, 281(45):34525-34536.

Yang et al., "cDNA Cloning, Genomic Structure, Chromosomal Mapping, and Functional Expression of a Novel Human Alanine Aminotransferase," Genomics, Mar. 1, 2002, 79(3):445-450.

Zhang et al., "Metabolic characteristics of recombinant Chinese hamster ovary cells expressing glutamine synthetase in presence and absence of glutamine," Cytotechnology, 2006, 51(1):21-28.

Fu et al., "Direct interaction and cooperative role of tumor suppressor p16 with band 3 (AEI)," FEBS Letters, 2005, 579(10):2105-2110.

Office Action dated Sep. 21, 2012 in U.S. Appl. No. 13/368,945.

Notice of Allowance dated Dec. 20, 2012 in U.S. Appl. No. 12/733,052.

Shibayama et al., "Effect of Methotrexate Treatment on Expression Levels of Organic Anion Transporter Polypeptide 2,P-Glycoprotein and Bile Salt Export Pump in Rats," Biol. Pharm. Bull., Mar. 2009, 32(3):493-496.

Final Office Action dated May 24, 2013 in U.S. Appl. No. 13/368,945.

Tanner et al., "The complete amino acid sequence of the human erythrocyte membrane anion-transport protein deduced from the cDNA sequence," Biochem. J., 1988, 256:703-712.

Beckmann et al., "Coexpression of band 3 mutants and Rh polypeptides: differential effects of band 3 on the expression of the Rh complex containing D polypeptide and the Rh complex containing CcEe polypeptide," Blood, Apr. 15, 2001, 97(8):2496-2505.

Han et al., "Regulation of TauT by cisplatin in LLC-PK1 renal cells," Pediatr. Nephrol., 2005, 20:1067-1072.

Ishiguro et al. "CO2 permeability and bicarbonate transport in microperfused interlobular ducts isolated from guinea-pig pancreas," Journal of Physiology, 2000, 528.2:305-315.

Mount et al., "The SLC26 gene family of multifunctional anion exchangers," Pflugers Arch.—Eur. J. Physiol., 2004, 447:710-721.

Pushkin et al., "SLC4 base (HCO-3, CO-23) transporters: classification, function, structure, genetic diseases, and knockout models," Am. J. Physiol. Renal Physiol., 2006, 290:F580-F599.

● DXB11s/AE1 HOST CELL
☐ DXB11s HOST CELL

Antibody Yield

AE1/CSAD ( n = 9 )
( 1098 ±139 ) mg/L

AE1/pPur ( n = 8 )
( 975 ±122 ) mg/L t Test    P<0.05

Survival Ratio

AE1/CSAD ( n = 9 )
( 69 ± 4 ) %

AE1/pPur ( n = 8 )
( 56 ± 4 ) % t Test    P<0.01

METHOD FOR PRODUCING A CELL CAPABLE OF HIGH-YIELD PRODUCTION OF HETEROPROTEINS

CROSS-REFERENCE TO RELATED APPLICATIONS

This application is a National Stage application of PCT/JP2010/057030, filed Apr. 21, 2010, which claims priority from Japanese application JP 2009-103596, filed Apr 22, 2009.

TECHNICAL FIELD

The present invention relates to a method for producing a cell capable of high-yield production of heteroproteins.

BACKGROUND ART

When proteins useful as pharmaceuticals are produced with the recombinant DNA technique, use of animal cells enables complicated post-translational modification and folding which prokaryotic cells can not perform. Therefore, animal cells are frequently used as host cells for producing recombinant proteins.

Recently, a large number of biopharmaceuticals, such as antibodies and physiologically active proteins, have been developed. Techniques that permit efficient production of recombinant proteins by animal cells lead to cost reduction of biopharmaceuticals and promise their stable supply to patients.

Under these circumstances, a method of protein production with higher production efficiency is desired.

It has been known that the number of copies of dihydrofolate reductase (DHFR) gene is amplified (gene amplification) in cells by methotrexate (MTX), whereby the cells become MTX-resistant. Widely used in industrial production is a method for increasing the amount of useful protein production, in which plasmids having a gene of the protein connected downstream of the DHFR gene are introduced into animal cells which are then cultured in an MTX-supplemented medium to induce gene amplification (Patent Document 1).

SUMMARY OF THE INVENTION

Problem for Solution by the Invention

An object of the present invention is to provide a method for producing a cell capable of high-yield production of heteroproteins.

Means to Solve the Problem

The present inventors devoted their full effort to solve the aforementioned problem. As a result, they found that host cells acquired MTX-resistance by strongly expressing a bicarbonate transporter in the cells, and cells that had come to produce an antibody following introduction of a gene of the antibody thereinto acquired MTX-resistance by strongly expressing a bicarbonate transporter in the cells, and further, an antibody production ability of antibody-producing cells in which a bicarbonate transporter was strongly expressed was improved by treating the cells with a high concentration of MTX; these findings led to completion of the present invention.

The present invention is summarized as follows.

(1) A method for producing a cell capable of high-yield production of a desired polypeptide, wherein a strongly bicarbonate transporter-expressing cell into which DNA encoding the desired polypeptide has been introduced is cultured in the presence of a high concentration of methotrexate and a cell capable of high-yield production of the desired polypeptide is selected from among surviving cells.

(2) The method according to (1) above, wherein DNA encoding dihydrofolate reductase is also introduced into the strongly bicarbonate transporter-expressing cell into which DNA encoding the desired polypeptide has been introduced.

(3) The method according to (2) above, wherein the strongly bicarbonate transporter-expressing cell into which DNA encoding the desired polypeptide has been introduced is a cell that is co-transformed with one molecule containing DNA encoding the desired polypeptide and DNA encoding dihydrofolate reductase.

(4) The method according to (3) above, wherein the molecule containing DNA encoding the desired polypeptide and DNA encoding dihydrofolate reductase is a vector.

(5) The method according to any one of (1) to (4) above, wherein the strongly bicarbonate transporter-expressing cell also strongly expresses alanine aminotransferase.

(6) A cell produced by a method according to any one of (1) to (5) above.

(7) A method for producing a desired polypeptide, wherein the cell according to (6) above is cultured.

(8) The method according to (7) above, wherein the desired polypeptide is an antibody.

(9) A method for producing a pharmaceutical product containing a polypeptide produced by the method according to (7) or (8).

(10) A method for enhancing the amount of polypeptide production by a strongly bicarbonate transporter-expressing cell into which DNA encoding a desired polypeptide has been introduced, the method comprising treating the cell is treated with a high concentration of methotrexate.

(11) The method according to (10) above, wherein DNA encoding dihydrofolate reductase is also introduced into the strongly bicarbonate transporter-expressing cell into which DNA encoding the desired polypeptide has been introduced.

(12) The method according to (11) above, wherein the strongly bicarbonate transporter-expressing cell into which DNA encoding the desired polypeptide has been introduced is a cell that is co-transformed with one molecule containing DNA encoding the desired polypeptide and DNA encoding dihydrofolate reductase.

(13) The method according to any one of (10) to (12) above, wherein the strongly bicarbonate transporter-expressing cell also strongly expresses alanine aminotransferase.

(14) A method for preparing a cell with a high survival rate in the culture in the presence of methotrexate at a high concentration, comprising allowing a cell to strongly express a bicarbonate transporter.

(15) A method for producing a cell capable of high-yield production of a desired polypeptide, wherein a strongly bicarbonate transporter-expressing cell into which DNA encoding the desired polypeptide has been introduced is cultured in the presence of methotrexate and a cell capable of high-yield production of the desired polypeptide is selected from among surviving cells.

(16) A method for enhancing the amount of polypeptide produced by a strongly bicarbonate transporter-expressing cell into which DNA encoding a desired polypeptide has been introduced, the method comprising treating the cell with methotrexate.

Effect of the Invention

The present invention enabled high-yield production of desired polypeptides including an antibody.

The present specification encompasses the contents disclosed in the specification and/or the drawings of Japanese Patent Application No. 2009-103596 based on which the present patent application claims priority.

The survival rates on day 7 of the culture were also characterized by $P<0.01$ (data not shown).

Figure 11:
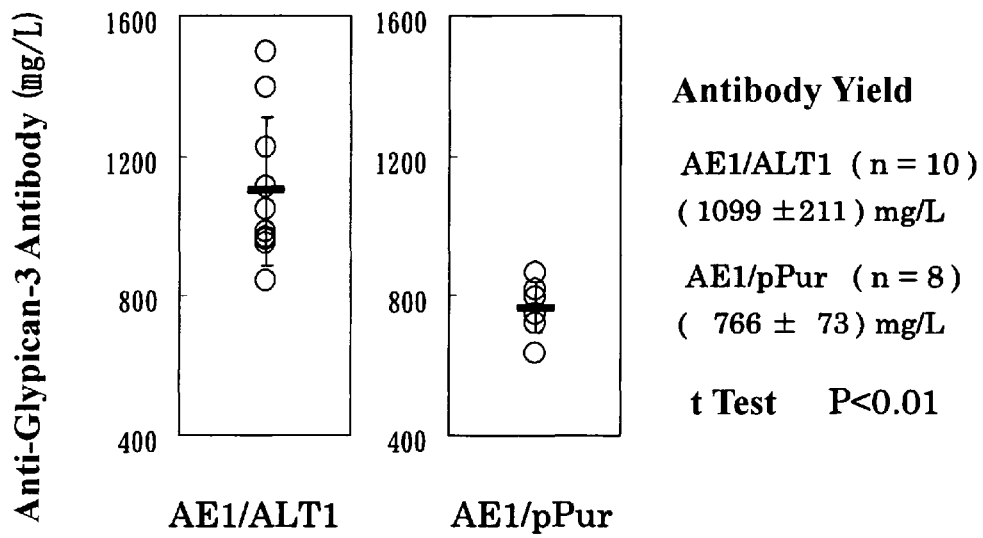

FIG. 11 is a plot of the amount of anti-glypican-3 antibody production on day of 8 fed-batch culture in a 50-mL shaker flask. The amount of an anti-glypican-3 antibody produced by an AE1/ALT co-expressing cell strain (n=10) which was obtained by introducing pPur-ALT1 into a pHyg-AE1-42 strain, or a pHyg-AE1-transformed cell capable of high-yield antibody production, was greater than that produced by an AE1/CSAD strain (n=9), and further, the amount of the anti-glypican-3 antibody produced by an AE1/ALT co-expressing cell strain was significantly greater than that produced by AE1/pPur co-expressing cells (n=8) which were obtained by introducing pPur into a pHyg-AE1-42 strain ($P<0.01$).

Figure 12:
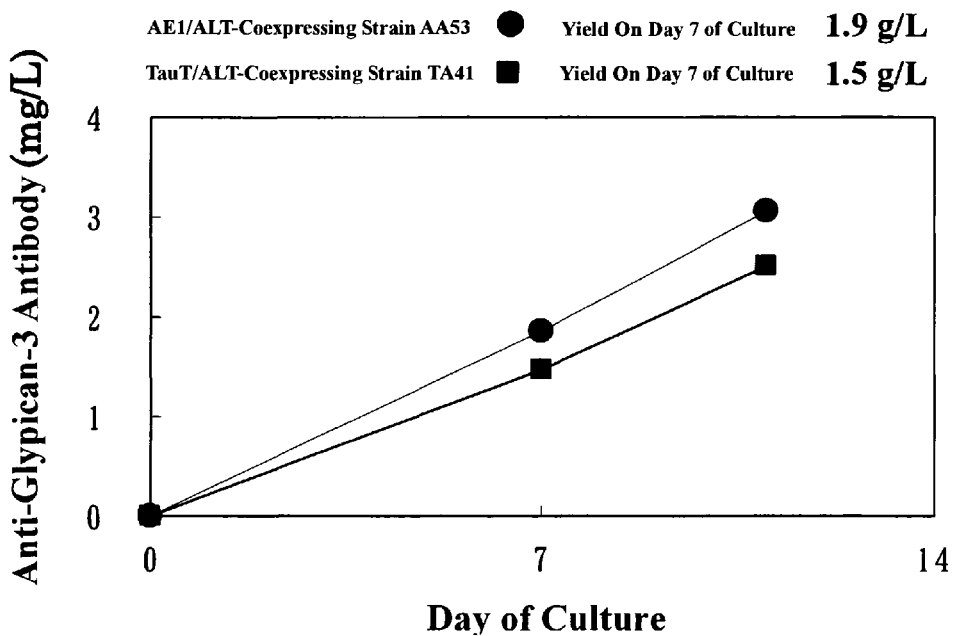

FIG. 12 is a graph showing the amount of an antibody produced by AA53, or an AE1/ALT1 co-expressing strain, during fed-batch culture in a 1 L jar. The amount of anti-glypican-3 antibody production on day 7 of the culture was 1.9 g/L.

EMBODIMENTS FOR CARRYING OUT THE INVENTION

Hereinbelow, embodiments of the present invention will be described in more detail.

The present invention provides a method for producing a cell capable of high-yield production of a desired polypeptide, wherein a strongly bicarbonate transporter expressing cell into which DNA encoding the desired polypeptide has been introduced is cultured in the presence of a high concentration of methotrexate (MTX) and a cell capable of high-yield production of the desired polypeptide is selected from among surviving cells.

According to the method of the present invention, a strongly bicarbonate transporter expressing cell into which DNA encoding the desired polypeptide has been introduced is cultured in the presence of a high concentration of MTX. The high concentration is a concentration at least twice the concentration at which an amplified gene is stably maintained during subculturing after ordinary selection of cells with MTX (about 20 nM for CHO cells), for example, a concentration at which 90% or more of cells of a strain having no bicarbonate transporter introduced are killed after 3 weeks of subculture, and although it varies depending on the type of cells, the concentration is generally appropriately 50 nM or more, preferably 80 nM or more, and further preferably 100 nM or more in the case of CHO DXB11s cells or other CHO cells used for manufacturing a recombinant protein.

DNA encoding the desired polypeptide is introduced into a strongly bicarbonate transporter expressing cell.

In the method of the present invention, the desired polypeptide is not particularly limited. The polypeptide may be any polypeptide such as an antibody (e.g., anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody, and the like) or a physiologically active protein (e.g., granulocyte-colony stimulating factor (G-CSF), granulocyte macrophage-colony stimulating factor (GM-CSF), erythropoietin, interferon, interleukin such as IL-1 or IL-6, t-PA, urokinase, serum albumin, blood coagulation factor, PTH, and the like). An antibody is particularly preferred, and may be any antibody such as a natural antibody, a low molecular sized antibody (e.g., Fab, scFv, sc(Fv)2), a chimeric antibody, a humanized antibody, etc.

A bicarbonate transporter is a membrane protein that has an antiport function, by which bicarbonate anions ($HCO_3^-$) or carbonate anions ($CO_3^{2-}$) are excreted whereas chloride anions and sulfate anions are taken up. A bicarbonate transporter may be exemplified by an SLC4 anion exchanger and an SLC26 anion exchanger.

An SLC4 anion exchanger is a membrane protein that regulates intracellular pH homeostasis and cell volume. At present, 10 kinds (SLC4A1 (AE1), SLC4A2 (AE2), SLC4A3 (AE3), SLC4A4 (NBCe 1), SLC4A5 (NBCe2), SLC4A7 (NBCn1), SLC4A8 (kNBC3), SLC4A9 (NBCn2), SLC4A10 (NBCn3), and SLC4A 11 (NaBC1)) of SLC4 families are known, and at least one kind of isoform exists. These SLC4 anion exchangers have different functions; for example, SLC4A1 (AE1), SLC4A2 (AE2), ALC4A3 (AE3), and ALC4A9 (NBCn2 or AE4) are non-Na$^+$-dependent, electrically-neutral exchangers for Cl$^-$ and HCO$_3^-$, ALC4A4 (NBCe1) and ALC4A5 (NBCe2) are electrogenic, ALC4A7 (NBCn1) is an electrically-neutral cotransporter for Na$^+$ and HCO$_3^-$, ALC4A8 (kNBC3) and ALC4A10 (NBCn3) are Na$^+$-dependent, electrically-neutral exchangers for Cl$^-$ and HCO$_3^-$, and ALC4A11 (NaBCl) is an electrogenic cotransporter for Na$^+$ and borate. The above SLC4 anion exchangers have a site-specific action. For example, in a case of AE1, AE1 present in polar epithelial cells contributes to transepithelial secretion and resorption of acids and bases whereas AE1 present in erythrocytes of trout promotes osmolyte transport. The SLC4 anion exchanger may be exemplified by SLC4A1 (AE1), SLC4A2 (AE2), SLC4A3 (AE3), SLC4A4 (NBCe1), SLC4A5 (NBCe2), SLC4A7 (NBCn1), SLC4A8 (kNBC3), SLC4A9 (NBCn2), SLC4A10 (NBCn3), and SLC4A11 (NaBCl), among which AE1 is preferable.

An SLC26 anion exchanger is a multifunctional membrane protein that acts in almost all organ systems. For the SLC26 anion exchanger, one that mediates antiport of sulfate anions, iodide anions, formate anions, oxalate anions, chloride anions, hydroxyl anions, bicarbonate anions and the like, and a chloride ion channel, or an anion-dependent molecular motor exist. The SLC26 anion exchanger is considered to be involved in homeostasis of various anions and 10 kinds (SLC26A1, SLC26A2, SLC26A3, SLC26A4, SLC26A5, SLC26A6, SLC26A7, SLC26A8, SLC26A9, and SLC26A11) of anion exchanger families have been known. For example, SLC26A3, SLC26A4, SLC26A6 and SLC26A9, which are transporters for hydroxyl anions and bicarbonate anions regulate pH inside as well as outside a membrane in a similar manner to an SLC4 anion exchanger. SLC26A1, SLC26A2, SLC26A4, SLC26A6, SLC26A9 and SLC26A11 are expressed in a kidney. SLC26A1 transports sulfate anions and oxalate anions whereas SLC26A6 mediates antiport of various anions in order to take up sodium chloride. SLC26A1, SLC26A4 and SLC26A6 and SLC26A5 become causative factors for nephrolithiasis, hypertension, and hearing loss, respectively. SLC26A7 is involved in acid-base homeostasis and blood pressure control in a similar manner to SLC26A4. The SLC26 anion exchanger may be exemplified by SLC26A1, SLC26A2, SLC26A3, SLC26A4, SLC26A5, SLC26A6, SLC26A7, SLC26A8, SLC26A9, and SLC26A11.

A cell which strongly expresses a bicarbonate transporter is not particularly limited as long as the cell has an increased expression level of a bicarbonate transporter compared to a corresponding natural cell. The natural cell is not particularly limited. A cell which is used as a host in the production of a recombinant protein (e.g., CHO cells) may be used.

A bicarbonate transporter to be strongly expressed in a cell may be derived from any organism and no particular limitation is imposed thereon. Specifically, the bicarbonate transporter may be derived from organisms including a human, rodents such as a mouse, a rat, and a hamster, mammals such as a chimpanzee, a cow, a horse, a dog, and a wolf, birds such as a chicken, fishes such as a zebrafish and an eel, and insects such as *Drosophila*; the bicarbonate transporter is preferably derived from a human, rodents, or the same species as the host cell. For example, in a case where the cell in which a bicarbonate transporter is to be strongly expressed is a Chinese hamster ovary cell (CHO cell), the bicarbonate transporter is preferably derived from a human or a hamster.

While a strongly bicarbonate transporter expressing cell can be any cell that may be eukaryotic cells including an animal cell, a plant cell, and yeast; or prokaryotic cells including *Escherichia coli* and *Bacillus subtilis*, a cultured cell employed as a host in the production of a recombinant protein is appropriate. Animal cells are preferable, among which mammalian cells such as such as a CHO cell and a COS cell are particularly preferable. The mammalian cells include cells of primates such as human and chimpanzee, rodents such as mouse, rat and hamster, and the like, and are preferably cells of human and rodents, with CHO cells being particularly preferred. Also, in order to produce a desired polypeptide, a dhfr-deficient CHO cell (for example, a DXB11 cell line of CHO cells or a DG44 cell line of CHO cells) is particularly preferable. Because a dhfr-deficient CHO cell is auxotrophic for hypoxanthine and thymidine, the cell cannot grow in a medium deprived of hypoxanthine and thymidine (hereinafter expressed as "medium without HT"); however, the cell becomes able to grow in the medium without HT once it is transformed with a recombinant vector containing a DHFR gene. Accordingly, it is convenient to use a dhfr-deficient CHO cell as a host because a transformed cell can be selected by utilizing the auxotrophy of the cell for hypoxanthine and thymidine.

As a cell which strongly expresses a bicarbonate transporter, a cell into which a bicarbonate transporter gene (e.g., SLC4 anion exchanger gene, SLC26 anion exchanger gene, etc.) has been artificially transferred may be given. A cell into which a bicarbonate transporter gene has been artificially transferred can be prepared by methods known to those skilled in the art. For example, such a cell may be prepared by incorporating a bicarbonate transporter into a vector and transforming the vector into a cell. Furthermore, the concept of "cells into which a bicarbonate transporter gene has been artificially transferred" encompasses herein cells in which an endogenous bicarbonate transporter gene has been activated by gene activation technology (see, for example, International Publication WO94/12650) so that the bicarbonate transporter is strongly expressed.

As an SLC4 anion exchanger gene to be transferred in a cell, any one of the following DNAs (a) to (e) encoding an SLC4 anion exchanger may be used.

(a) a DNA encoding a polypeptide having the amino acid sequence as shown in SEQ ID NO: 2;

(b) a DNA encoding a polypeptide which has an amino acid sequence derived from the amino acid sequence as shown in SEQ ID NO: 2 by substitution, deletion, addition and/or insertion of one or more amino acid residues and yet has SLC4 anion exchanger activity;

(c) a DNA encoding a polypeptide having 50% or more amino acid sequence homology with the amino acid sequence as shown in SEQ ID NO: 2 and yet having SLC4 anion exchanger activity;

(d) a DNA having the nucleotide sequence as shown in SEQ ID NO: 1;

(e) a DNA which hybridizes to a DNA complementary to a DNA having the nucleotide sequence as shown in SEQ ID NO: 1 under stringent conditions and yet encodes a polypeptide having SLC4 anion exchanger activity.

The concept of an SLC4 anion exchanger activity encompasses an activity to take up Cl$^-$ and SO$_4^{2-}$ present in the medium and excrete intracellular HCO$_3^-$ and borate in order to maintain intracellular pH homeostasis and cell volume.

The SLC4 anion exchanger activity can be measured as follows.

Cells in which SLC4 is functionally expressed are treated with BCECF-AM which is a pH-sensitive dye. Then, fluorescent intensity is compared between cells that have been perfused with a medium containing Cl⁻ and Na⁺ and cells that have been perfused with a medium free of Cl⁻ and Na⁺, whereby changes in intracellular pH (pHi) can be measured (Dahl N K. et.al., J Biol Chem 2003; 278:44949-44958; Fujinaga J. et.al., J Biol Chem 1999; 274:6626-6633).

In the present invention, a DNA encoding a polypeptide having the amino acid sequence of SEQ ID NO: 2 is advantageously used as a DNA encoding an SLC4 anion exchanger. Besides that, a DNA encoding a polypeptide having the amino acid sequence of SEQ ID NO: 2 in which one or a plurality (for example, several) of amino acid(s) is/are substituted, deleted, added, and/or inserted, and also having an SLC4 anion exchanger activity may be used. The amino acid sequence of SEQ ID NO: 2 is an amino acid sequence of human AE1. Aside from the sequence information of human AE1, the counterpart information about a mouse, a rat, a chimpanzee, a cow, a horse, a dog, a wolf, a chicken, a zebrafish, and the like has been registered as mouse; GenBank NM_011403, rat; GeneBank NM_012651, chimpanzee; GenBank XM_001151353, cow; GeneBank NM_181036, horse; GeneBank NM_001081788, dog; GenBank AB242566, wolf; GeneBank NM_001048031, chicken; GenBank NM_205522, and zebrafish; GenBank NM_198338. Thus, AE1 as described above can also be used. Other SLC4 anion exchangers can also be used since the sequence information thereof has been registered in various databases.

The polypeptide which has an amino acid sequence derived from the amino acid sequence as shown in SEQ ID NO: 2 by substitution, deletion, addition and/or insertion of one or more amino acid residues and yet has SLC4 anion exchanger activity is functionally equivalent to an SLC4 anion exchanger derived from human, mouse, rat, chimpanzee, cow, horse, dog, wolf, chicken or zebrafish (hereinafter sometimes referred to as "SLC4 anion exchanger derived from human or the like"). Such a polypeptide encompasses, for example, mutants of the SLC4 anion exchanger derived from human or the like. In Example described below, a mutant in which four out of 911 amino acids were replaced (L88R, E693G, V712A and H834Y) was used.

As methods well-known to those skilled in the art for preparing polypeptides functionally equivalent to a specific polypeptide, methods of introducing mutations into polypeptides may be given. For example, those skilled in the art could prepare polypeptides functionally equivalent to the SLC4 anion exchanger derived from human or the like by appropriately introducing mutations into amino acids of the SLC4 anion exchanger derived from human or the like by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature.

Specific examples of polypeptides functionally equivalent to the SLC4 anion exchanger derived from human or the like include, but are not limited to, a polypeptide having an amino acid sequence derived from the amino acid sequence (e.g., SEQ ID NOS: 2) of the SLC4 anion exchanger derived from human or the like by deletion of one or more amino acids, preferably 1-30 amino acids, more preferably 1-10 amino acids; a polypeptide having an amino acid sequence derived from the amino acid sequence of the SLC4 anion exchanger derived from human or the like by addition of one or more amino acids, preferably 1-30 amino acids, more preferably 1-10 amino acids; and a polypeptide having an amino acid sequence derived from the amino acid sequence of the SLC4 anion exchanger derived from human or the like by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, G, H, K, S and T), amino acids with an aliphatic side chain (G, A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

As one example of the polypeptide in which one or more amino acid residues are added to the SLC4 anion exchanger derived from human or the like, a fusion polypeptide comprising the SLC4 anion exchanger derived from human or the like may be given. Such a fusion polypeptide is composed of the SLC4 anion exchanger derived from human or the like and other polypeptide fused thereto. Such a fusion polypeptide may be prepared by linking a gene encoding the SLC4 anion exchanger derived from human or the like in frame with a gene encoding the other polypeptide, transferring the resultant DNA into an expression vector and expressing the DNA in a host cell. Techniques known to those skilled in the art may be used. There is no limitation on the polypeptide to be fused to the SLC4 anion exchanger derived from human or the like.

Examples of polypeptides to be fused to the SLC4 anion exchanger derived from human or the like include, but are not limited to, FLAG (Hopp, T. P. et al., BioTechnology (1988) 6, 1204-1210), 6×His comprising six histidine (H is) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the SLC4 anion exchanger derived from human or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence (e.g., SEQ ID NOS: 1) of the SLC4 anion exchanger derived from human or the like based on that DNA sequence or a part thereof, and isolate polypeptides functionally equivalent to the SLC4 anion exchanger derived from human or the like from that DNA.

Hybridization conditions for isolating a DNA encoding a polypeptide functionally equivalent to the SLC4 anion exchanger derived from human or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the SLC4 anion exchanger derived from human or the like in the amino acid sequence. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the SLC4 anion exchanger derived from human or the like, a DNA encoding the polypeptide can be used in the present invention. For example, when the polypeptide of the present invention is expressed in a prokaryote (e.g., *Escherichia coli*), a methionine reside is added to the N-terminus of the initial amino acid sequence of the polypeptide. When the polypeptide is expressed in a eukaryote (e.g., a mammalian cell), the N-terminal signal sequence is removed. These polypeptides can be used in the present invention.

In the present invention, as a DNA encoding an SLC4 anion exchanger, a DNA having the nucleotide sequence as shown in SEQ ID NO: 1 may be used. Alternatively, a DNA which hybridizes to a DNA complementary to a DNA having the nucleotide sequence as shown in SEQ ID NO: 1 under stringent conditions and yet encodes a polypeptide having SLC4 anion exchanger activity, may be used. SEQ ID NO. 1 shows the nucleotide sequence of human AE1. Aside, from the sequence information of human AE1, the counterpart information about a mouse, a rat, a chimpanzee, a cow, a horse, a dog, a wolf, a chicken, a zebrafish, and the like has been registered as mouse; GenBank NM_011403, rat; GenBank NM_012651, chimpanzee; GenBank XM_001151353, cow; GenBank NM_181036, horse; GenBank NM_001081788, dog; GenBank AB242566, wolf; GeneBank NM_001048031, chicken; GenBank NM_205522, and zebrafish; GenBank NM_198338. Thus, AE1 as described above can also be used. Other SLC4 anion exchangers can also be used since the sequence information thereof has been registered in various databases.

The DNA encoding an SLC4 anion exchanger can be used in the in vivo or in vitro production of a desired polypeptide as described above. Further, the DNA encoding an SLC4 anion exchanger may be used in the creation of a cell which strongly expresses an SLC4 anion exchanger. The DNA encoding an SLC4 anion exchanger may take any form as long as it is capable of encoding an SLC4 anion exchanger. That is, the DNA may be, for example, a cDNA synthesized from mRNA, a genomic DNA or a chemically synthesized DNA. It should be noted that, as long as the DNA is capable of encoding an SLC4 anion exchanger, the DNA may have any nucleotide sequence based on the degeneracy of genetic codes.

The DNA encoding an SLC4 anion exchanger may be prepared by methods known to those skilled in the art. For example, the DNA may be prepared by preparing a cDNA library from a cell expressing an SLC4 anion exchanger and performing hybridization using a part of the DNA sequence of an SLC4 anion exchanger (e.g., SEQ ID NO: 1) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding an SLC4 anion exchanger by preparing RNA from a cell expressing an SLC4 anion exchanger, synthesizing oligo DNA molecules based on the DNA sequence of an SLC4 anion exchanger (e.g., SEQ ID NO: 1), and performing PCR using the oligo DNA molecules as primers to thereby amplify a cDNA encoding an SLC4 anion exchanger.

Further, by determining the nucleotide sequence of the resultant cDNA, it is possible to determine the translation region encoding an SLC4 anion exchanger and to obtain the amino acid sequence of the SLC4 anion exchanger. Further, by screening a genomic library using the resultant cDNA as a probe, it is possible to isolate a genomic DNA.

Specifically, the following procedures may be used. First, mRNA is isolated from cells, tissues or the like expressing an SLC4 anion exchanger. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., *E. coli*), followed by selection of resultant colonies to thereby obtain a desired recombinant vector. The nucleotide sequence of the DNA of interest may be confirmed by a known method such as the dideoxynucleotide chain termination method.

Further, a nucleotide sequence of higher expression efficiency can be designed for the DNA encoding an SLC4 anion exchanger by considering the frequency of codon usage in the host to be used for expression (Grantham, R. et al., Nucleic Acids Research (1981) 9, p. 43-74). Further, the DNA encoding an SLC4 anion exchanger can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding an SLC4 anion exchanger also includes a DNA which hybridizes to a DNA having the nucleotide sequence as shown in SEQ ID NO: 1 under stringent conditions and encodes a polypeptide functionally equivalent to an SLC4 anion exchanger.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the SLC4 anion exchanger derived from human or the like. The DNA encoding an SLC4 anion exchanger also includes a DNA which encodes a polypeptide functionally equivalent to the SLC4 anion exchanger derived from human or the like and has high identity with a DNA encoding the SLC4 anion exchanger derived from human or the like. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (http://www.ncbi.nlm.nih.gov.).

A bicarbonate transporter gene to be incorporated into a cell may be an SLC26 anion exchanger gene. Information of a nucleotide sequence of an SLC26 anion exchanger gene and an amino acid encoded by the gene has been registered as GenBank AF331525 (human putative SLC26A9), GenBank NM_052934 (human SLC26A9 variant 1), GenBank NM_134325 (human SLC26A9 variant 2), GenBank NM_134420 (mouse SLC26A6), GenBank NM_177243 (mouse SLC26A9), GenBank AY240025 (Drosophila Slc26d9702), GenBank AY240023 (Drosophila Slc26d6928), GenBank AY240022 (Drosophila Slc26d6125), GenBank AY240021 (Drosophila Slc26d5002), and GenBank AB084425 (eel Slc26A6). Thus, the SLC26 anion exchanger gene described as above can be used.

The DNA encoding an SLC4 anion exchanger may be inserted into a vector.

When the host cell to be used is *E. coli*, it is preferable that the vector has a replication origin ("ori") so that the vector is largely amplified in *E. coli* (e.g., JM109, DH5α, HB101 and XL1-Blue) and prepared in large quantity, and also genes for selecting transformed *E. coli* (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in *E. coli* is intended, the expression vector preferably has the above-described features so that the vector is amplified in *E. coli*, and it also preferably has a promoter which allows efficient expression in *E. coli* such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5x-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of *E. coli*, pelB signal sequence (Lei, S. P. et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than *E. coli* is used, vectors useful for producing a desired polypeptide include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovairus expression system from GIBCO BRL; pBacPAK8), plant-derived expression vectors (e.g., pMH1, pMH2), animal virus-derived expression vectors (e.g., pHSV, pMV, pAdexLcw), retrovirus-derived expression vectors (e.g., pZIpneo), yeast-derived expression vectors (e.g., *Pichia* Expression Kit fron Invitrogen; pNV11; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF 1αpromoter (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, pBK-CMV, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene and *E. coli* xanthine-guanine phosphoribosyl transferase (Ecogpt) gene.

The host cell into which the DNA encoding a bicarbonate transporter (which may be incorporated in a vector) is transferred is not particularly limited. For example, *E. coli* or various animal cells may be used. If a DNA encoding a desired polypeptide is transferred into a host cell into which a DNA encoding a bicarbonate transporter is transferred, this host cell can express the bicarbonate transporter strongly, which leads to an increased production of the desired polypeptide. Into the host cell into which a DNA encoding a bicarbonate transporter is transferred, a DNA encoding CSAD or ALT (which may be incorporated into a vector) may be further transferred. By transferring a DNA encoding a desired polypeptide and a DNA encoding CSAD or ALT into a host cell into which a DNA encoding a bicarbonate transporter is transferred, the yield of the desired polypeptide can be increased. For the production of the polypeptide, there are in vivo and in vitro production systems. Examples of in vitro production systems include systems using eukaryotes and systems using prokaryotes.

When a desired polypeptide is produced using a cell into which a bicarbonate transporter gene has been artificially transferred, the order of the transfer of a bicarbonate transporter gene and the transfer of a gene encoding a desired polypeptide is not particularly limited. A gene encoding a desired polypeptide may be transferred after the transfer of a bicarbonate transporter gene. Alternatively, a bicarbonate transporter gene may be transferred after the transfer of a gene encoding a desired polypeptide. It is also possible to transfer a bicarbonate transporter gene and a gene encoding a desired polypeptide simultaneously.

A bicarbonate transporter gene and a gene encoding a desired polypeptide may be transferred simultaneously in a single vector. Alternatively, they may be transferred separately using a plurality of vectors.

Preferably, the cell which strongly expresses a bicarbonate transporter further expresses alanine aminotransferase (ALT) strongly.

ALT is fundamentally known as an enzyme that produces glutamate by transferring an amino group from alanine to 2-oxoglutarate. If the reaction of biosynthesizing pyruvate and glutamate from alanine could be promoted by strongly expressing ALT in host cells such as CHO cells, the products might be utilized in metabolism during a TCA cycle and glucose production by glycogenesis, and this might improve cell culture behavior, leading to high-yield production of the desired polypeptide.

The strongly ALT expressing cells are not particularly limited as long as they are capable of ALT expression at higher levels than natural cells. Natural cells include, but are not particularly limited to, cells that are used as hosts in the production of recombinant proteins and may be exemplified by CHO cells.

As a cell which strongly expresses ALT, a cell into which an ALT gene has been artificially transferred may be given. A cell into which an ALT gene has been artificially transferred can be prepared by methods known to those skilled in the art. For example, such a cell may be prepared by incorporating an ALT gene into a vector and transforming the vector into a cell. Furthermore, the concept of "cells into which an ALT gene has been artificially transferred" encompasses herein cells in which an endogenous ALT gene has been activated by gene activation technology (see, for example, International Publication WO94/12650) so that ALT is strongly expressed.

As ALT to be strongly expressed in a cell, ALT derived from any organism may be used. Specifically, ALTs derived from human, mouse, rat, dog, African clawed frog, fruit fly, nematode, Japanese rice, *Cyanidioschyzon merolae*, *Saccharomyces cerevisiae*, *Ashbya gossypii*, *Candida albicans*, *Schizosaccharomyces pombe*, *Aspergillus nidulans*, *Aspergillus fumigatus*, *Aspergillus oryzae*, *Cryptococcus neoformans*, *Dictyostelium discoideum*, *Trypanosoma brucei*, *Leishmania major*, *Entamoeba histolytica* and *Trypanosoma cruzi* are known and can be used. Preferably, ALT derived from human, a rodent or the same species as the host cell may be used. For example, when the cell which is allowed to strongly express ALT is Chinese hamster ovary cells (CHO cells), ALT is preferably derived from human or hamster. For ALT in humans, mice, and yeast, variants (ALT1 and ALT2) exist. ALT2 has 80% or greater homology to ALT1 at the amino acid level. ALT1 was forcedly expressed in the Examples and Referential Examples described later.

As an ALT gene to be strongly expressed in a cell, any one of the following DNAs (a2) to (e2) encoding ALT may be used.

(a2) a DNA encoding a polypeptide having the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C. KEGG/ENZYME: 2.6.1.2/*Saccharomyces cerevisiae*: YLR089C. KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950. KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140;

(b2) a DNA encoding a polypeptide which has an amino acid sequence derived from the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/Dictyostelium discoideum: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 by substitution, deletion, addition and/or insertion of one or more (e.g., several) amino acid residues and yet has ALT activity;

(c2) a DNA encoding a polypeptide having 70% or more amino acid sequence homology with the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770 KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/Dictyostelium discoideum: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 and yet having ALT activity;

(d2) a DNA having the nucleotide sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111C, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/Dictyostelium discoideum: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430 KEGG/ENZYME: 2.6.1.2/*Trypanosoma cruzi*: 510889.120 or KEGG/ENZYME: 2.6.1.2/*Trypanosoma cruzi*: 510889.140;

(e2) a DNA which hybridizes to a DNA complementary to a DNA having the nucleotide sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_

6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 under stringent conditions and yet encodes a polypeptide having ALT activity.

The concept of an ALT activity encompasses an enzyme activity to catalyze transfer of an amino group between an amino acid and an α-keto acid.

The ALT activity can be measured as follows.

An ALT activity level is determined by a reagent for automated analyzer for measuring alanine aminotransferase (Runpia liquid S-ALT, approval number 20900AMZ00597000) and the method taught by Rajamohan F. et.al., Protein Expression and Purification (2006) 48, 81-89.

In the present invention, as a gene encoding ALT, a DNA encoding a polypeptide having the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/Cyanidioschyzon merolae: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 may be used. Alternatively, a DNA encoding a polypeptide which has an amino acid sequence derived from the amino acid sequence described above by substitution, deletion, addition and/or insertion of one or more amino acid residues and yet has ALT activity may be used. SEQ ID NOs: 3 and 4 in the sequence listing respectively show the nucleotide sequence and amino acid sequence of the gene encoding human ALT1 (KEGG/ENZYME: 2.6.1.2/*Homo sapiens* (human): 2875).

The polypeptide which has an amino acid sequence derived from the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089C, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/Trypanosoma brucei: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 by substitution, deletion, addition and/or insertion of one or more amino acid residues and yet has ALT activity is functionally equivalent to ALT derived from human, mouse, rat, dog, African clawed frog, fruit fly, nematode, Japanese rice, *Cyanidioschyzon merolae*, *Saccharomyces cerevisiae*, *Ashbya gossypii*, *Candida albicans*, *Schizosaccharomyces pombe*, *Aspergillus nidulans*, *Aspergillus fumigatus*, *Aspergillus oryzae*, *Cryptococcus neoformans*, *Dictyostelium discoideum*, *Trypanosoma brucei*, *Leishmania major*, *Entamoeba histolytica* or *Trypanosoma cruzi* (hereinafter sometimes referred to as "ALT derived from human or the like"). Such a polypeptide encompasses, for example, mutants of ALT derived from human or the like. In Example and Referential Examples described below, a mutant in which four out of 496 amino acids were replaced (R53S, Q72R, F286S and M332K) was used.

As methods well-known to those skilled in the art for preparing polypeptides functionally equivalent to a specific polypeptide, methods of introducing mutations into polypeptides may be given. For example, those skilled in the art could prepare polypeptides functionally equivalent to ALT derived from human or the like by appropriately introducing mutations into amino acids of ALT derived from human or the like by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, TA (1985)

Proc Natl Acad Sci USA. 82, 488-492; Kunkel (1988) Methods Enzymol. 85, 2763-2766). Mutations in amino acids may also occur in nature.

Specific examples of polypeptides functionally equivalent to the ALT derived from human or the like include, but are not limited to, a polypeptide having an amino acid sequence derived from the amino acid sequence (e.g., the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111C, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630 KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140) of the ALT derived from human or the like by deletion of one or more amino acids, preferably 1-30 amino acids, more preferably 1-10 amino acids; a polypeptide having an amino acid sequence derived from the amino acid sequence of the ALT derived from human or the like by addition of one or more amino acids, preferably 1-30 amino acids, more preferably 1-10 amino acids; and a polypeptide having an amino acid sequence derived from the amino acid sequence of the ALT derived from human or the like by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, G, H, K, S and T), amino acids with an aliphatic side chain (G, A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

As one example of the polypeptide in which one or more amino acid residues are added to the ALT derived from human or the like, a fusion polypeptide comprising the ALT derived from human or the like may be given. Such a fusion polypeptide is composed of the ALT derived from human or the like and other polypeptide fused thereto. Such a fusion polypeptide may be prepared by linking a gene encoding the ALT derived from human or the like in frame with a gene encoding the other polypeptide, transferring the resultant DNA into an expression vector and expressing the DNA in a host cell. Techniques known to those skilled in the art may be used. There is no limitation on the polypeptide to be fused to the ALT derived from human or the like.

Examples of polypeptides to be fused to the ALT derived from human or the like include, but are not limited to, FLAG (Hopp, T. P. et al., BioTechnology (1988) 6, 1204-1210), 6×His comprising six histidine (His) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin. (HA), immunoglobulin constant region, β-galactosidase and maltose-binding protein (MBP).

A commercially available gene encoding such polypeptide is fused to the gene encoding the ALT derived from human or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence (e.g., the DNA sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111C, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/EN- ZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140) of the ALT derived from human or the like based on that DNA sequence or a part thereof, and isolate polypeptides functionally equivalent to the ALT derived from human or the like from that DNA.

Hybridization conditions for isolating a DNA encoding a polypeptide functionally equivalent to the ALT derived from human or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the ALT derived from human or the like in the amino acid sequence. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the ALT derived from human or the like, a DNA encoding the polypeptide can be used in the present invention. For example, when the polypeptide of the present invention is expressed in a prokaryote (e.g., *Escherichia coli*), a methionine reside is added to the N-terminus of the initial amino acid sequence of the polypeptide. When the polypeptide is expressed in a eukaryote (e.g., a mammalian cell), the N-terminal signal sequence is removed. A DNA encoding such a polypeptide can be used in the present invention.

In the present invention, as a DNA encoding ALT, a DNA having the nucleotide sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640 KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630 KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 may be used. Alternatively, a DNA which hybridizes to a DNA complementary to a DNA having the nucleotide sequence described above under stringent conditions and yet encodes a polypeptide having ALT activity, may be used.

The DNA encoding ALT can be used in the in vivo or in vitro production of a desired polypeptide as described above. Further, the DNA encoding ALT may be used in the creation of a cell which strongly expresses ALT. The DNA encoding ALT may take any form as long as it is capable of encoding ALT. That is, the DNA may be, for example, a cDNA synthesized from mRNA, a genomic DNA or a chemically synthesized DNA. It should be noted that, as long as the DNA is capable of encoding ALT, the DNA may have any nucleotide sequence based on the degeneracy of genetic codes.

The DNA encoding ALT may be prepared by methods known to those skilled in the art. For example, the DNA may be prepared by preparing a cDNA library from a cell expressing ALT and performing hybridization using a part of the DNA sequence of ALT (e.g., the DNA sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa* japonica (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium* gossypii): AGOS_AGR085W, KEGG/ENZYME: 2.6.1.2/ Candida albicans: CaO19_346, KEGG/ENZYME: 2.6.1.2/ Schizosaccharomyces pombe: SPBC582.08, KEGG/ENZYME: 2.6.1.2/Aspergillus nidulans: AN1923.2, KEGG/ ENZYME: 2.6.1.2/Aspergillus fumigatus: AFUA_ 6G07770, KEGG/ENZYME: 2.6.1.2/Aspergillus oryzae: AO090003000164, KEGG/ENZYME: 2.6.1.2/Cryptococcus neoformans JEC21: CNG01490, KEGG/ENZYME: 2.6.1.2/ Dictyostelium discoideum: DDB_0232139, KEGG/ENZYME: 2.6.1.2/Trypanosoma brucei: Tb927.1.3950, KEGG/ ENZYME: 2.6.1.2/Leishmania major: LmjF12.0630, KEGG/ENZYME: 2.6.1.2/Entamoeba histolytica: 233.t00009, KEGG/ENZYME: 2.6.1.2/Entamoeba histolytica: 24.t00016, KEGG/ENZYME: 2.6.1.2/Trypanosoma cruzi: 506529.420, KEGG/ENZYME: 2.6.1.2/Trypanosoma cruzi: 506529.430, KEGG/ENZYME: 2.6.1.2/ Trypanosoma cruzi: 510889.120 or KEGG/ENZYME: 2.6.1.2/Trypanosoma cruzi: 510889.140) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding ALT by preparing RNA from a cell expressing ALT, synthesizing oligo DNA molecules based on the DNA sequence of ALT (e.g., the DNA sequence of KEGG/ENZYME: 2.6.1.2/Homo sapiens (human): 2875, KEGG/ENZYME: 2.6.1.2/Homo sapiens (human): 84706, KEGG/ENZYME: 2.6.1.2/Mus musculus (mouse): 76282, KEGG/ENZYME: 2.6.1.2/Mus musculus (mouse): 108682, KEGG/ENZYME: 2.6.1.2/Rattus norvegicus (rat): 81670, KEGG/ENZYME: 2.6.1.2/Canis familiaris (dog): 609510, KEGG/ENZYME: 2.6.1.2/Xenopus laevis (African clawed frog): 444533, KEGG/ENZYME: 2.6.1.2/Drosophila melanogaster (fruit fly): Dmel_CG1640 KEGG/ENZYME: 2.6.1.2/Caenorhabditis elegans (nematode): C32F10.8, KEGG/ENZYME: 2.6.1.2/Oryza sativa japonica (Japanese rice): 4342210, KEGG/ENZYME: 2.6.1.2/Oryza sativa japonica (Japanese rice): 4348524, KEGG/ENZYME: 2.6.1.2/Cyanidioschyzon merolae: CMM066C, KEGG/ENZYME: 2.6.1.2/Saccharomyces cerevisiae: YLR089c, KEGG/ENZYME: 2.6.1.2/Saccharomyces cerevisiae: YDR111c, KEGG/ENZYME: 2.6.1.2/Ashbya gossypii (Eremothecium gossypii): AGOS_AGR085W, KEGG/ENZYME: 2.6.1.2/Candida albicans: CaO19_346, KEGG/ENZYME: 2.6.1.2/Schizosaccharomyces pombe: SPBC582.08, KEGG/ENZYME: 2.6.1.2/Aspergillus nidulans: AN1923.2, KEGG/ENZYME: 2.6.1.2/Aspergillus fumigatus: AFUA_ 6G07770, KEGG/ENZYME: 2.6.1.2/Aspergillus oryzae: AO090003000164, KEGG/ENZYME: 2.6.1.2/Cryptococcus neoformans JEC21: CNG01490, KEGG/ENZYME: 2.6.1.2/ Dictyostelium discoideum: DDB_0232139, KEGG/ENZYME: 2.6.1.2/Trypanosoma brucei: Tb927.1.3950, KEGG/ ENZYME: 2.6.1.2/Leishmania major: LmjF12.0630, KEGG/ENZYME: 2.6.1.2/Entamoeba histolytica: 233.t00009, KEGG/ENZYME: 2.6.1.2/Entamoeba histolytica: 24.t00016, KEGG/ENZYME: 2.6.1.2/Trypanosoma cruzi: 506529.420, KEGG/ENZYME: 2.6.1.2/Trypanosoma cruzi: 506529.430, KEGG/ENZYME: 2.6.1.2/ Trypanosoma cruzi: 510889.120 or KEGG/ENZYME: 2.6.1.2/Trypanosoma cruzi: 510889.140), and performing PCR using the oligo DNA molecules as primers to thereby amplify a cDNA encoding ALT.

Further, by determining the nucleotide sequence of the resultant cDNA, it is possible to determine the translation region encoding ALT and to obtain the amino acid sequence of ALT. Further, by screening a genomic library using the resultant cDNA as a probe, it is possible to isolate a genomic DNA.

Specifically, the following procedures may be used. First, mRNA is isolated from cells, tissues or the like expressing ALT. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., E. coli), followed by selection of resultant colonies to thereby obtain a desired recombinant vector. The nucleotide sequence of the DNA of interest may be confirmed by a known method such as the dideoxynucleotide chain termination method.

Further, a nucleotide sequence of higher expression efficiency can be designed for the DNA encoding ALT by considering the frequency of codon usage in the host to be used for expression (Grantham, R. et al., Nucleic Acids Research (1981) 9, p. 43-74). Further, the DNA encoding ALT can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding ALT also includes a DNA which hybridizes to a DNA complementary to a DNA having the nucleotide sequence of KEGG/ENZYME: 2.6.1.2/Homo sapiens (human): 2875, KEGG/ENZYME: 2.6.1.2/Homo sapiens (human): 84706, KEGG/ENZYME: 2.6.1.2/Mus musculus (mouse): 76282, KEGG/ENZYME: 2.6.1.2/Mus musculus (mouse): 108682, KEGG/ENZYME: 2.6.1.2/Rattus norvegicus (rat): 81670, KEGG/ENZYME: 2.6.1.2/Canis familiaris (dog): 609510, KEGG/ENZYME: 2.6.1.2/Xenopus laevis (African clawed frog): 444533, KEGG/ENZYME: 2.6.1.2/Drosophila melanogaster (fruit fly): Dmel_CG1640, KEGG/ENZYME: 2.6.1.2/Caenorhabditis elegans (nematode): C32F10.8, KEGG/ENZYME: 2.6.1.2/Oryza sativa japonica (Japanese rice): 4342210, KEGG/ENZYME: 2.6.1.2/Oryza sativa japonica (Japanese rice): 4348524, KEGG/ENZYME: 2.6.1.2/Cyanidioschyzon merolae: CMM066C, KEGG/ENZYME: 2.6.1.2/Saccharomyces cerevisiae: YLR089c, KEGG/ENZYME: 2.6.1.2/Saccharomyces cerevisiae: YDR111C, KEGG/ENZYME: 2.6.1.2/Ashbya gossypii (Eremothecium gossypii): AGOS_AGR085W, KEGG/ENZYME: 2.6.1.2/Candida albicans: CaO19_346, KEGG/ENZYME: 2.6.1.2/Schizosaccharomyces pombe: SPBC582.08, KEGG/ENZYME: 2.6.1.2/Aspergillus nidulans: AN1923.2, KEGG/ENZYME: 2.6.1.2/Aspergillus

*fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/,ENZYME: 2.6.1.2/ *Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 under stringent conditions and encodes a polypeptide functionally equivalent to ALT.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the ALT derived from human or the like. The DNA encoding ALT also includes a DNA which encodes a polypeptide functionally equivalent to the ALT derived from human or the like and has high identity with a DNA encoding the ALT derived from human or the like. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (http://www.ncbi.nlm.nih.gov/.).

A DHFR gene may be introduced into a strongly bicarbonate transporter expressing cell together with DNA encoding the desired polypeptide. The number of copies of DHFR gene is amplified (gene amplification) in cells by MTX, whereby the cells take on MTX-resistant. The strongly bicarbonate transporter expressing cell may be obtained by co-transformation with one molecule (for example, a vector) containing DNA encoding the desired polypeptide and DNA encoding DHFR. When a recombinant vector in which DNA encoding the desired polypeptide is connected to a DHFR gene is introduced into cells and the cells thus obtained are cultured in a medium in the presence of MTX, cells capable of high-yield production of the desired polypeptide by gene amplification can be obtained. The DHFR gene may be derived from any various organisms, and their DNA sequences are publicly known (mouse: GenBank V00734, rat: GenBank AF318150, and human: GenBank J00140). Hence, the DHFR gene may be prepared in accordance with such available information and introduced into a vector. Further, a commercially available expression vector in which the DHFR gene is introduced (pOptiVEC™-TOPO (registered trademark) vector, a product of Invitrogen Corporation) can also be used.

When a cell into which a bicarbonate transporter gene is artificially introduced is employed as a host, DNA encoding the desired polypeptide and DNA encoding DHFR may be introduced into the cell after the bicarbonate transporter gene is introduced, or, in the other way around, the bicarbonate transporter gene may be introduced into the cell after DNA encoding the desired polypeptide and DNA encoding DHFR are introduced. Alternatively, the bicarbonate transporter gene, DNA encoding the desired polypeptide, and DNA encoding DHFR may be simultaneously introduced into the cell.

The bicarbonate transporter gene (and also the ALT gene, in some cases) and DNA encoding the desired polypeptide may be simultaneously introduced by a single vector, or each independently introduced by using a plurality of vectors.

Furthermore, DNA encoding the desired polypeptide and the DHFR gene may be introduced into a single vector or different vectors. In order to efficiently establish a strain capable of high-yield production by gene amplification, it is preferable to introduce DNA encoding the desired polypeptide and the DHFR gene into a single vector. In order to increase an amplification efficiency of the gene, it is preferable to connect the DHFR gene downstream of a promoter having a low transcription efficiency (for example, a SV40 promoter), and connect DNA encoding the desired polypeptide downstream of a promoter having a high transcription efficiency (for example, a CMV promoter, a SRα promoter, or an EF-1α promoter). When DNA encoding the desired polypeptide and the DHFR gene are introduced into different vectors, the vectors may be introduced into a host cell by co-transfection. In this case, the vector into which DNA encoding the desired polypeptide is incorporated is preferably introduced into the host cell in an excess amount (normally, approximately twice to 40 times in excess) over the vector into which the DHFR gene is incorporated.

For construction of a polypeptide expression vector in CHO cells, utilization of a CMV immediate-early enhancer/promoter region, a typical Kozak sequence (−6 GCCR (R=A/G) CCAUGG+4) (SEQ ID NO: 5), and a drug-resistance marker (such as neomycin, hygromycin, or puromycin), as well as addition of a secretion signal peptide (such as MGWSCIILFLVATATGVHS (SEQ ID NO: 6)) to the N-terminal side may be considered.

The expression vector may be cleaved with an appropriate restriction enzyme into a linear form before it is introduced into host cells. An expression unit of a gene of interest can be easily incorporated into the chromosome in the host cells by preparing the vector into a linear form. A gene transfer method is not particularly limited, and it may be any method such as a calcium phosphate method, a DEAE dextran method, a lipofection method, or an electroporation method. Multiple copies can be introduced by carrying out gene transfer with NUCLEOFECTOR (a product of Amaxa Biosystems).

After carrying out gene transfer into host cells, the cells are cultured in a selection medium, whereby cells into which a gene of interest has been introduced may be selected. For example, when DNA encoding the desired polypeptide is inserted in a vector having a drug-resistance gene, and host cells are transformed with the vector thus obtained and then are cultured in the medium containing a drug, surviving cells can be selected as transformed cells. Furthermore, when DNA encoding the desired polypeptide is inserted in a vector having a DHFR gene, and dhfr-deficient CHO cells, which serve as host cells, are transformed with the vector thus obtained and then cultured in a medium without HT, surviving cells can be selected as transformed cells. For the medium, a CHO—S—SFMII/CD-CHO mixed medium (a product of Invitrogen Corporation) and the like may be used. The transformed cells are continuously cultured and the amount of polypeptide of interest produced is measured after an appropriate time has passed (normally, approximately on the $14^{th}$ to $21^{st}$ day). Subsequently, cells capable of high-yield production are subjected to MTX treatment. The transformed cells to be subjected to MTX treatment are preferably capable of not only high-yield polypeptide production but also rapid proliferation. Proliferation rates can be compared by measuring the number of viable cells that have been subcultured.

The MTX treatment refers to, for example, culturing cells (preferably subculturing) in a medium to which a high concentration of MTX has been added. The high concentration is a concentration at least twice the concentration at which an amplified gene is stably maintained during subculturing after ordinary selection of cells with MTX (about 20 nM for CHO cells), for example, a concentration at which 90% or more of cells of a strain having no bicarbonate transporter introduced are killed after 3 weeks of subculture, and although it varies depending on the type of cells, the concentration is generally appropriately 50 nM or more, preferably 80 nM or more, and further preferably 100 nM or more in the case of CHO DXB11s cells or other CHO cells used for manufacturing a recombinant protein. Seven to 35 days are appropriate as a culture period; it is preferably 14 to 28 days, and more preferably 21 to 28 days.

When transformed cells are cultured in a medium to which a high concentration of MTX has been added, the concentration of MTX may be increased in a stepwise fashion. For example, the cells are cultured in a medium containing MTX at a concentration of 10 nM for 14 to 21 days, and then cultured in a medium containing MTX at a concentration of 100 nM for 14 to 28 days.

A strain capable of high-yield production may be selected in every step of culturing with the concentration of MTX being changed. Also, when cell proliferation is no longer observed due to culturing in the medium to which a high concentration of MTX has been added, cell proliferation may be recovered by putting cells back to a medium to which a low concentration of MTX has been added and then continuing culturing in that medium.

For the medium to which a high concentration of MTX is added, a CHO—S—SFMII/CD-CHO mixed medium (a product of Invitrogen Corporation) and the like can be used.

Even when a transformed strain is nearly uniform before it is subjected to MTX treatment, it will lose uniformity after MTX treatment because it will acquire diversity through the treatment. The total amount of polypeptide produced by a group of ununiform cells becomes greater than the amount produced by the nearly uniform strain before MTX treatment. It is possible to clone only a strain capable of high-yield production from a group of cells that have acquired diversity. For example, limiting dilution employing a 96-well plate and single cell cloning accomplished by a cell sorter are effective. A publicly known method can be employed for either of these methods.

The strongly bicarbonate transporter expressing cell of the present invention has an excellent MTX-resistant ability as revealed by the Examples described later, and therefore, the cell can be selected at a higher concentration of MTX than the normal concentration at which selection is performed.

From the group of cells of the present invention obtained through treatment with a high concentration of MTX as described above, a strain capable high-yield production of the desired polypeptide that is impossible or very difficult to obtain by normal MTX treatment can be obtained efficiently in a large number. Hence, the strongly bicarbonate transporter expressing cell of the present invention is extremely useful as a transformed cell to be used for MTX selection.

Accordingly, the present invention also provides a cell capable of high-yield production of the desired polypeptide that is produced by the methods described above. The cell can be a group of nonuniform cells or a cloned uniform strain.

The present invention provides a method for producing a polypeptide, wherein the cell produced by the methods described above is cultured. Furthermore, a desired polypeptide can be prepared by using a cell in which an endogenous gene has been activated by gene activation technology (see, for example, International Publication WO94/12650) so that a desired polypeptide has been produced.

For culturing the cell, media used in conventional cell culture (preferably, animal cell culture) may be used. These media usually contain amino acids, vitamins, lipid factors, energy sources, osmotic regulators, iron sources and pH regulators. The contents of these components are usually as follows: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH regulators 1-10000 mg/L. However, the contents are not limited to these ranges and may be appropriately selected depending on the type of the cell to be cultured, the type of the desired polypeptide, and so on.

In addition to these components, trace metal elements, surfactants, growth cofactors, nucleosides, and the like may be added. The contents of these components are usually as follows: trace metal elements 0.00001-200 mg/L, surfactants 0-5000 mg/L, growth cofactors 0.05-10000 μg/L and nucleosides 0.001-50 mg/L. However, the contents are not limited to these ranges and may be appropriately selected depending on the type of the cell to be cultured, the type of the desired polypeptide, and so on.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$ and ascorbic acid, preferably, biotin, folic acid, lipoic acid, nicotinamide, calcium pantothenate, pyridoxal hydrochloride, riboflavin, thiamine hydrochloride, vitamin $B_{12}$ and ascorbic acid; lipid factors, such as choline chloride, choline tartrate, linoleic acid, oleic acid and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium hydrogencarbonate, calcium chloride, sodium dihydrogenphosphate, HEPES and MOPS, preferably, sodium hydrogencarbonate. Culture media containing any of these components may be given as examples.

Besides the above components, there may be added trace metal elements, such as copper sulfate, manganese sulfate, zinc sulfate, magnesium sulfate, nickel chloride, tin chloride, magnesium chloride and sodium subsilicate, preferably, copper sulfate, zinc sulfate and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α, ethanolamine hydrochloride, sodium selenite, retinoic acid and putrescine dihydrochloride, preferably, sodium selenite, ethanolamine hydrochloride, recombinant IGF-1 and putrescine dihydrochloride; and nucleosides, such as deoxyadenosine, deoxycytidine, deoxyguanosine, adenosine, cytidine, guanosine and uridine. In preferable examples of above media, antibiotics, such as streptomycin, penicillin-G potassium and gentamicin, and pH-indicators, such as Phenol Red, may be contained.

The pH of the medium varies depending on the cell to be cultured. Generally, pH 6.8-7.6 is appropriate. In many cases, pH 7.0-7.4 is appropriate.

It is also possible to use a commercial medum for animal cell culture, e.g., D-MEM (Dulbecco's Modified Eagle Medium), D-MEM/F-12 1:1 Mixture (Dulbecco's Modified Eagle Medium Nutrient Mixture F-12), RPMI1640, CHO—S—SFMII (Invitrogen), CHO—SF (Sigma-Aldrich), EX-CELL 301 (JRH Biosciences), CD-CHO (Invitrogen), IS CHO—V (Irvine Scientific), PF-ACF—CHO (Sigma-Aldrich) or the like. Alternatively, the medium may be a serum-free medium.

When the cell is a CHO cell, the CHO cell may be cultured by methods known to those skilled in the art. For example, the CHO cell may be cultured usually in an atmosphere with a $CO_2$ concentration in the gas phase of 0 to 40%, preferably 2 to 10%, at 30 to 39° C., preferably about 37° C.

An appropriate culture period for producing a desired polypeptide using the cell is usually 1 day to 3 months, preferably 1 day to 2 months, more preferably 1 day to 1 month.

With respect to various culture devices for animal cell culture, a fermentor type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device, or the like may be used.

Culture may be performed by any culture method such as batch culture, fed-batch culture or continuous culture. Preferably, fed-batch culture or continuous culture is used. Fed-batch culture is more preferred.

When the polypeptide produced according to the method of the present invention has a biological activity useful as a pharmaceutical, it is possible to produce a pharmaceutical by mixing this polypeptide with pharmaceutically acceptable carriers or additives and formulating into a preparation.

Specific examples of pharmaceutically acceptable carriers and additives include water, organic solvents that are pharmaceutically acceptable, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methylcellulose, ethyl cellulose, xanthan gum, gum Arabic, casein, agar-agar, polyethylene glycol, diglycerin, glycerin, propylene glycol, petrolatum, paraffin, stearyl alcohol, stearic acid, human serum albumin (HSA), mannitol, sorbitol, lactose, and surfactants that are acceptable as pharmaceutical additives.

Actual additives may be selected from the above-mentioned additives singly or in combination according to the dosage form of the therapeutic of the present invention, but are not limited to those listed above. For example, when a polypeptide is used in an injectable formulation, the purified polypeptide may be dissolved in a solvent such as physiological saline, buffer or a glucose solution, and then an adsorption inhibitor such as Tween 80, Tween 20, gelatin or human serum albumin may be added to the solution. Alternatively, a freeze-dried agent may be used to prepare a dosage form which is dissolved and reconstituted prior to use. Examples of the excipient useful for freeze-drying include sugar alcohols and saccharides such as mannitol and glucose.

Effective doses of the polypeptide may be appropriately selected depending on the type of the polypeptide, the type of the disease to be treated or prevented, the age of the patient, the severity of the disease, etc. For example, when the polypeptide is anti-glypican antibody, the effective dose of anti-glypican antibody (e.g., in the case of anticancer agent) is selected within a range of 0.001 mg to 1000 mg per kg of body weight per administration. Alternatively, a dose of 0.01-100000 mg/body may be selected per patient. However, effective dose is not limited to these ranges.

The polypeptide may be administered either orally or parenterally, but parenteral administration is preferred. Specifically, injection (e.g., systemic or local administration by intravenous injection, intramuscular injection, intraperitoneal injection, subcutaneous injection, etc.), transnasal administration, transpulmonary administration, transdermal administration and the like may be enumerated.

In another embodiment of the present invention, there is provided a method for enhancing the amount of polypeptide production by the strongly bicarbonate transporter expressing cell into which DNA encoding the desired polypeptide has been introduced, the method comprising treating the cell with a high concentration of MTX.

As another embodiment of the present invention, there is provided a method for preparing a cell with a high survival rate in the culture in the presence of methotrexate at a high concentration, comprising allowing a cell to strongly express a bicarbonate transporter.

The present invention encompasses a method for producing a cell capable of high-yield production of a desired polypeptide, wherein a strongly bicarbonate transporter-expressing cell into which DNA encoding the desired polypeptide has been introduced is cultured in the presence of methotrexate and a cell capable of high-yield production of the desired polypeptide is selected from among surviving cells.

In addition, the present invention also encompasses a method for enhancing the amount of polypeptide produced by a strongly bicarbonate transporter-expressing cell into which DNA encoding a desired polypeptide has been introduced, the method comprising treating the cell with methotrexate.

In the present invention, the concept of "cells into which DNA has been transferred" encompasses not only cells into which exogenous DNA has been incorporated by genetic recombination technology; but also cells in which endogenous DNA has been activated by gene activation technology (see, for example, International Publication WO94/12650) so that expression of a protein corresponding to the endogenous DNA or transcription of the DNA has been initiated or increased.

EXAMPLES

Hereinbelow, the present invention will be described in more detail with reference to the following Examples. It should be noted that these Examples are provided only for illustrating the present invention and not for limiting the scope of the present invention.

Example 1

Figure 1:
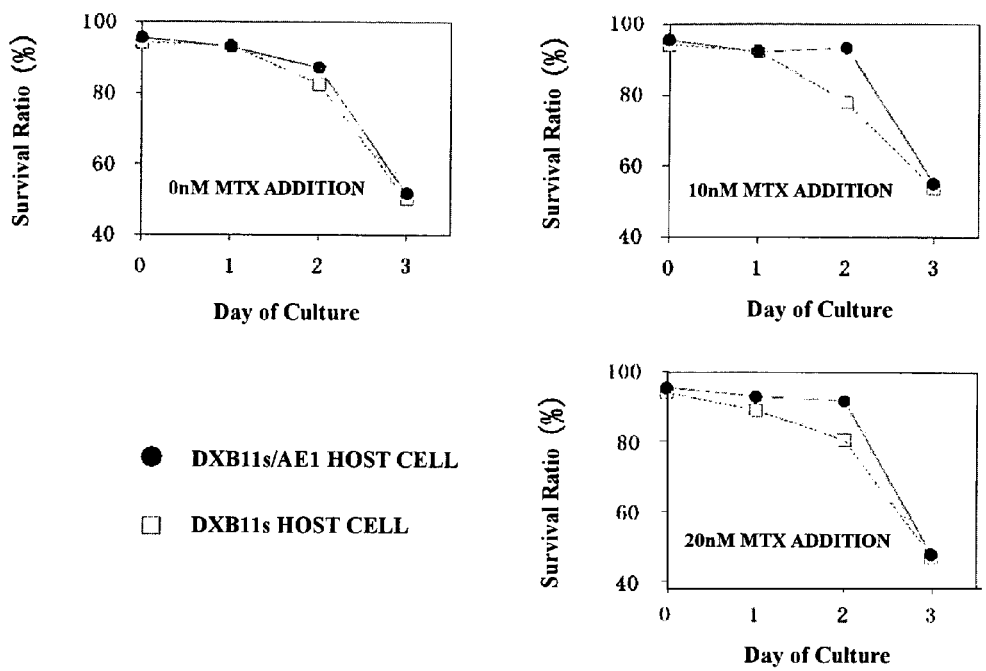
FIG. 1 shows host cells in which an anion exchanger (AE1) is strongly expressed take on MTX-resistance.
Figures 5, 6:
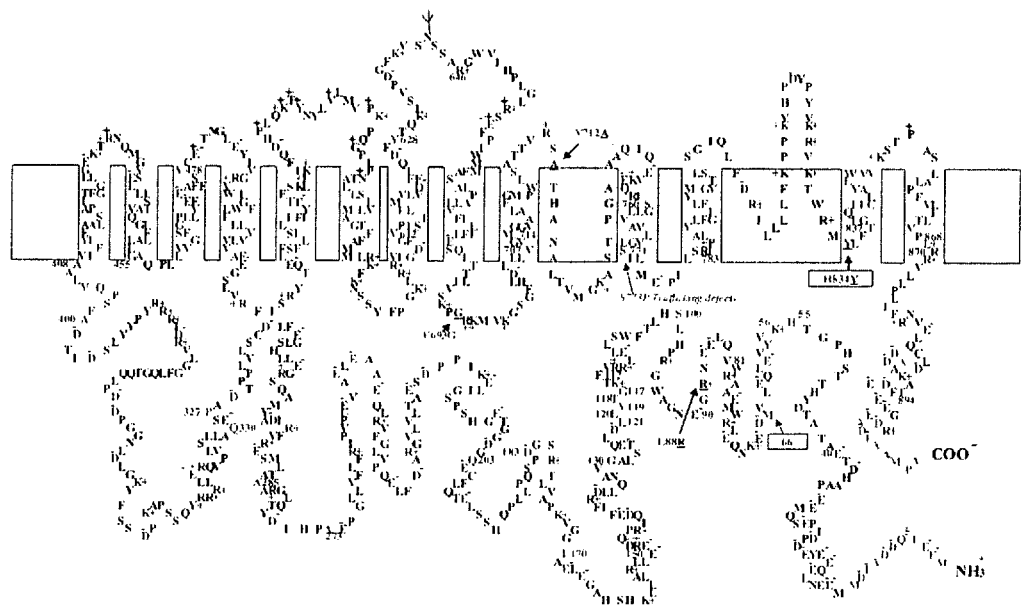
FIG. 5 shows an AE1 membrane topology produced based on a transmembrane domain and direction predicted from an amino acid sequence of human hepatic cell-derived AE1 as obtained by TMpred program with reference to FIG. 1 in Exo Physiol 91.1 pp. 153-161, 2006, Seth L. Alper.
FIG. 6 shows a plasmid for Hygromycin-selection, in which human AE1 (911 amino acids) has been expressed.

Acquisition of MTX Resistance of Host Cells by Anion Exchanger (AE1) Introduction The pHyg-AE1 expression plasmid (Referential Example 2 and FIG. 5 set forth below) was introduced into DXB11S host cells by electroporation to prepare DXB11S/AE1 host cells where AE1 was strongly expressed, and their MTX sensitivity was compared with that of the parent strain DXB11S host cells. While neither of the host cells can survive in a HT-free medium due to their HT supplement requirement, the reductions in their survival rate under the condition where no MTX was added to a HT-free medium were comparable, as shown in FIG. 1. However, under the condition where 10 nM or 20 nM MTX was added to the HT-free medium, the survival rate of the DXB11S/AE1 host cells after 2 days of culture was higher than that of the DXB11S host cells, suggesting that DXB11 S/AE1 host cells had acquired MTX resistance.

Example 2

Figure 2:
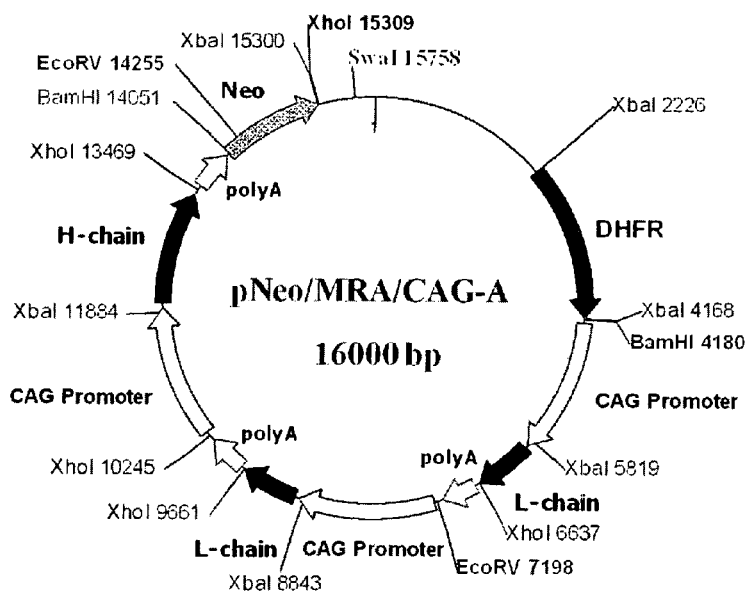
FIG. 2 is an anti-IL-6R antibody expression plasmid (pNeo/MRA/CAG-A).
Figure 3:
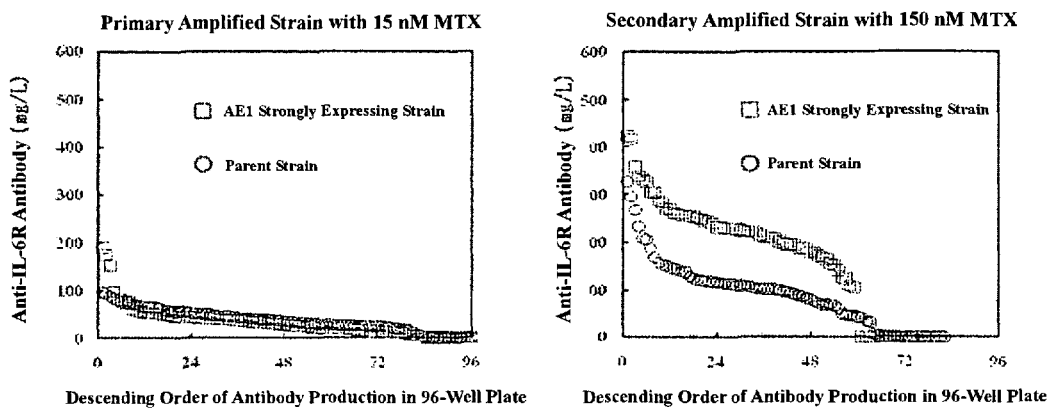
FIG. 3 shows that a strain more highly producing antibody than a parent strain DXB11y host is obtained by using DXB11y/AE1 host cells.

Construction of Antibody Producing Strain by DXB11S/AE1 Host Cells that Acquired MTX Resistance The DXB11S/AE1 host cells constructed from DXB11S host cells acclimated to CHO—S—SFM II were acclimated to CS(CHO—S—SFM IUCD-CHO) to prepare DXB11y/AE1 host cells, and further, CS acclimated DXB11y host cells, the parent strain of the DXB11S host cells, were used as, control cells to enable transfection in a Fetuin-free medium, and thus a new strain of antibody producing cells was constructed. One microgram of an anti-IL-6R antibody (tocilizumab, trade name: ACTEMRA (registered trademark)) expression plasmid (pNeo/MRA/CAG-A) (FIG. 2) was introduced into 15×10e5 host cells by Amaxa nucleofector (Nucleofector kit V, program U-030). Following replacement with a HT-free CS medium after 6 hours of nuclefection, 7500 cells were seeded to each well of a 96 half-well plate and allowed to stand in a 5% CO2 incubator at 37° C. for 1 week and, thereafter, MTX was added to make a final concentration of 15 nM and the mixture was allowed to stand for an additional 1 week. For their expansion culture, the cells in each well were transferred to a 96-well plate containing 100 µl of a HT-free 15 nM MTX/CS medium and statically cultured for another 8 days (200 µl in total). After the expansion culture, in order to evaluate antibody production, 150 µl of the cell solution was transferred to a 24-well plate containing 700 µl of CS medium, and batch culture was performed at 160 rpm for 14 days. To the remaining cell solution (50 µl), 150 µl of HT-free 15 nM MTX/CS medium was added and expansion culture by subculture was continued. After 14 days, the amount of antibody production in the 24-well batch culture was determined (plot of primary amplified strain production in FIG. 3), to select top 5 strains of each culture. Expansion culture of the top 5 strains was performed until 6-well plate, and thereafter, 1000 cells were seeded to each well of a 96 half-well plate and statically cultured for 14 days in the presence of a HT-free 150 nM MTX/CS medium (100 µl in total) to perform secondary amplification of the antibody expression unit. For expansion culture of the secondarily amplified cells, a maximum of 20 strains of highly proliferative cells were selected from each well (no more than 100 stains in total for each culture), and the cells were transferred from the 96 half-well plate to a 96-well plate containing 100 µl of a HT-free 150 nM MTX/CS medium and statically cultured for another 11 days (200 µl in total). In the same manner as described above, 150 µl of the cell solution was subjected to 24-well batch culture and the antibody production of proliferated cells was evaluated, whereby it was shown that cell strains highly producing antibody can be obtained in large numbers by strain construction using DXB11 S/AE1 host cells (plot of secondary amplified strain production in FIG. 3).

Example 3

Figure 4:
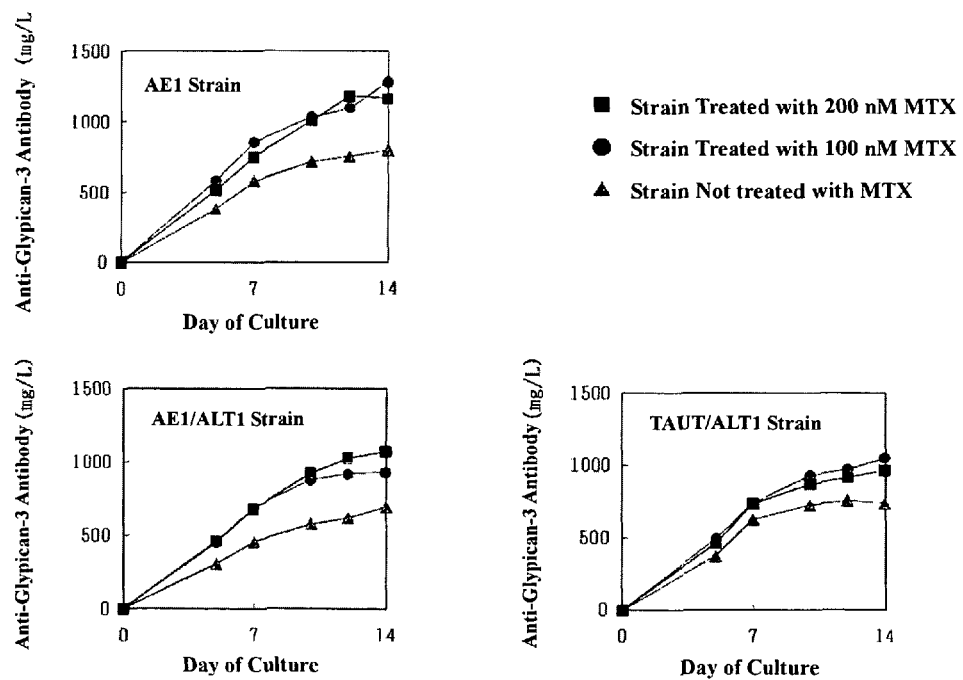
FIG. 4 shows that antibody production of an AE1 strongly expressing strain increases after treatment with high concentration of MTX.

Increase in Antibody Production from AE1 Strongly Expressing Antibody Producing Strain by Treatment with High Concentration of MTX After static culture in a 5% CO2 incubator at 37° C. for 24 days (subculture by centrifugation for medium replacement at day 10 and day 18) in the presence of MTX at high concentration (100 nM or 200 nM), the MTX concentration was returned to the initial value (20 nM), and the cells were statically cultured for 22 days, thereby restoring cell proliferation (4 passages by T25 flask static culture, 1 passage by 6-well plate suspension, and 1 passage by shaker flask suspension). Suspension production Fed-Batch culture was performed for 14 days using a shaker, and the antibody production was compared with that of a control, i.e., a strain not treated with high concentration of MTX (cells subcultured in the presence of 20 nM MTX). In an AE strain where AE1 was strongly expressed (the DXB11 S/AE1 host cells acquiring MTX resistance in Example 1) and an AE1/ALT1 coexpression strain (AE1/ALT1 coexpression strain in Referential Example 2 set forth below), antibody production was found to increase by treatment with high concentrations of MTX (FIG. 4), as in a TAUT/ALT1 coexpression strain where TAUT was strongly expressed (TAUT/ALT1 coexpression strain in Example 2 of WO2009/020144).

These results suggest that by artificially expressing the anion exchanger gene (AE1), cells acquire MTX resistance and that even higher antibody production can be realized by treatment with high concentration of MTX.

The present invention is applicable to all types of antibody producing cells.

Referential Example 1

Cloning of a Human Hepatic Cell Anion Exchanger (Anion Exchanger 1, Band 3) Gene Using a commercial Human Liver QUICK-Clone cDNA (Clontech Laboratories, Inc.) as a template, an Anion Exchanger (AE1) gene derived from a human liver was obtained by a PCR method. The gene thus cloned was sequenced to confirm that it encoded AE1 in view of its homology with a published human AE1. The AE1 gene thus obtained had mutations at eight sites in the sequence of 2733 bases (t263g, t357c, a645t, a672c, c951t, a2078g, t2195c, c2500t) and coded for 911 amino acids including four different amino acids (L88R, E693G, V712A, H834Y). However, because a product obtained by the gene was predicted to be a transporter having 13 transmembrane domains (FIG. 5), the gene was used for cell modulation as an AE1 gene derived from a human liver.

Referential Example 2

Figure 7:
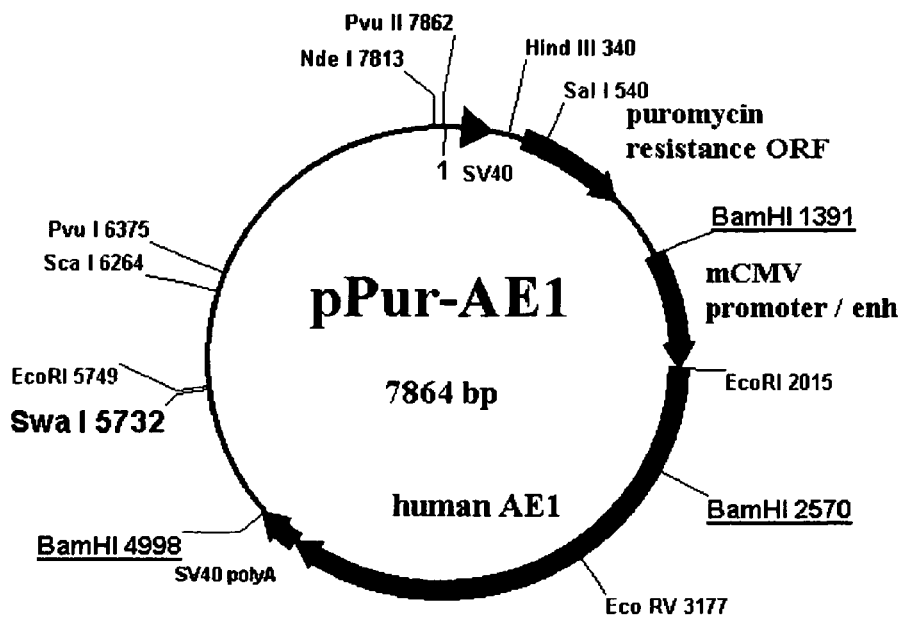
FIG. 7 shows a plasmid for Puromycin-selection, in which human AE1 (911 amino acids) has been expressed.
Figure 8:
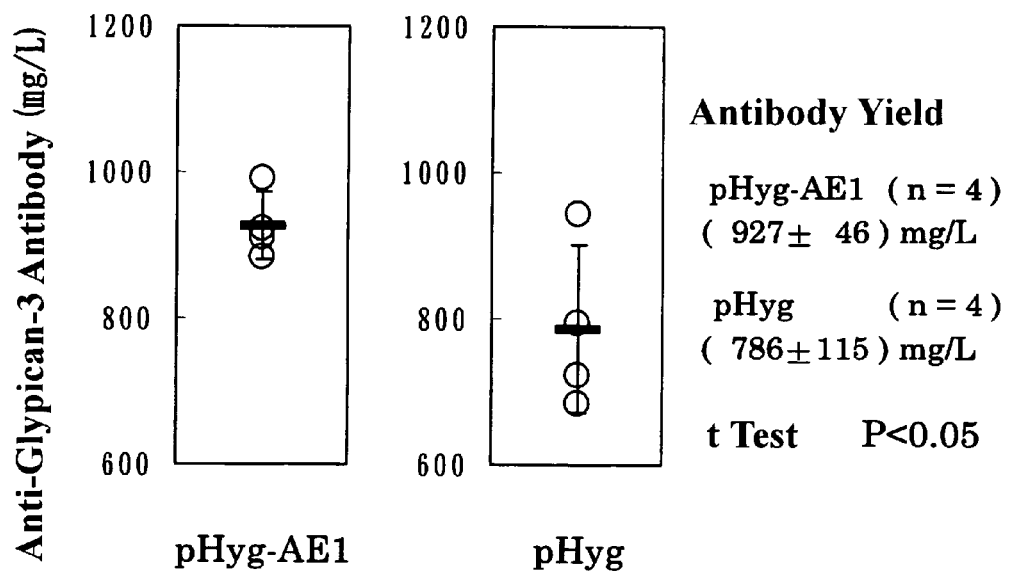
FIG. 8 is a plot of the amount of anti-glypican-3 antibody production on day 12 of fed-batch culture in a 50-mL shaker flask. The amount of an anti-glypican-3 antibody produced by pHyg-AE1-transformed cells (n=4) was significantly greater than that produced by pHyg-transformed cells (n=4) ($P<0.05$).

Increase in the Amount of Antibody Production by Introduction of a Human Anion Exchanger Gene By adding a Kozak sequence to the human AE1 gene obtained by PCR cloning in Referential Example 1 (which is hereinafter called AE1), pHyg-AE1 (FIG. 6) and pPur-AE1 (FIG. 7) were constructed as CMV promoter expression plasmids. The pHyg-AE1 or pHyg expression plasmids that did not contain the AE1 gene (which was obtained by first introducing Hygromycin-resistance gene expression units derived from pTK5 provided by Clontech Laboratories, Inc. into pSV2-dhfr plasmids (ATCC No. 37146) and then removing the dhfr expression units from the constructed plasmids) were introduced into anti-glypican-3 antibody-producing CHO cells as a parent strain (see International Publication WO 2006/006693) by electroporation. Then, strains that exhibited high proliferation in static culture in the presence of Hygromycin (200 µg/ml) were selected. After amplification, a total RNA was prepared from the pHyg-AE1 strains, and five strains expressing human AE1 at high levels were selected by a TaqMan method. Further, a comparison was made for the amount of antibody production between pHyg-transformed cells as a control (four strains) and four strains of human AE1-transformed cells that proliferated at a level equivalent to that observed with control during shake culture. During fed-batch culture in a 50-ml shaker flask under the condition of $2\times10^5$ cells/mL in an initial stage, the amount of an anti-glypican-3 antibody produced by pHyg-AE1-transformed cells (four strains) on day 12 after initiation of the shake culture was significantly greater than that produced by pHyg-transformed cells (four strains) (t-test: $P<0.05$, FIG. 8).

Figure 9:
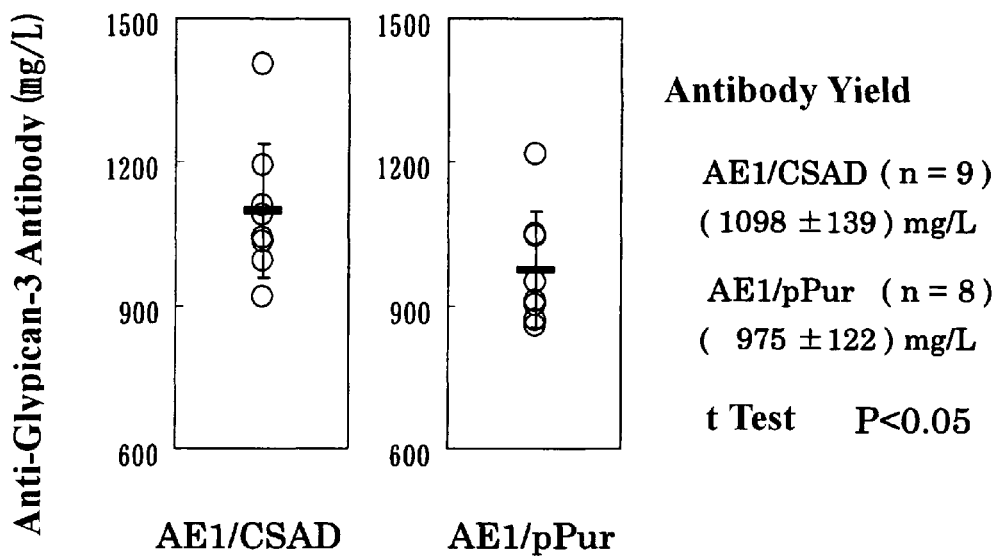
FIG. 9 is a plot of the amount of anti-glypican-3 antibody production on day 10 of fed-batch culture in a 50-mL shaker flask. The amount of an anti-glypican-3 antibody produced by an AE1/CSAD co-expressing cell strain (n=9) which was obtained by introducing pPur-CSAD into a pHyg-AE1-42 strain, or a pHyg-AE1-transformed cell capable of high-yield antibody production, was significantly greater than that produced by AE1/pPur co-expressing cells (n=8) which were obtained by introducing pPur into a pHyg-AE1-42 strain ($P<0.05$).
Figure 10:
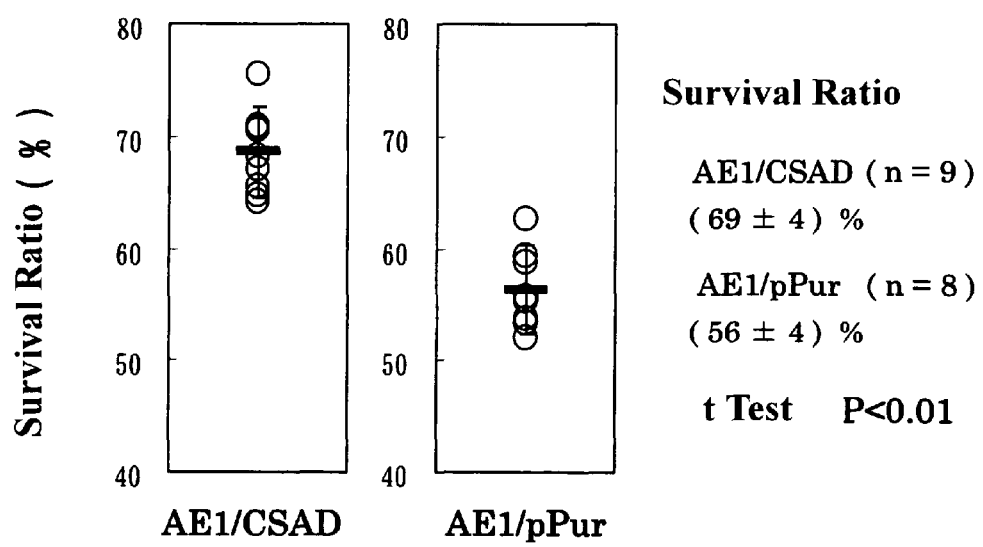
FIG. 10 is a plot of survival rates on day 10 of fed-batch culture in a 50-mL shaker flask. The survival rate of an AE1/CSAD co-expressing cell strain (n=9) which was obtained by introducing pPur-CSAD into a pHyg-AE1-42 strain, or a pHyg-AE1-transformed cell capable of high-yield antibody production, was significantly higher than that of AE1/pPur co-expressing cells (n=8) which were obtained by introducing pPur into a pHyg-AE1-42 strain ($P<0.01$).

Then, using as a parent strain the AE1 expressing strain that produced the largest amount of an antibody among the four pHyg-AE1-transformed strains, pPur-CSAD or a cysteine sulfinic acid decarboxylase (CSAD) expression plasmid containing a Puromycin-resistance gene (see Example 2, FIG. 7 in WO2008/114673), pPur-ALT1 or an alanine aminotransferase (ALT1) expression plasmid containing Puromycin-resistance gene (see Example 2, FIG. 1 in WO2009/020144), and a control plasmid pPur (pPUR, Puromycin resistance expression vector, provided by Clontech Laboratories, Inc.) were introduced by electroporation. Then, strains that exhibited high proliferation in static culture in the presence of Puromycin (6 µg/ml) were selected. After amplification, a total RNA was prepared from the strains thus selected. Then, AE1/CSAD co-expressing strains (nine strains), AE1/ALT1 co-expressing strains (10 strains), and AE1/pPur co-expressing strains (eight strains), which expressed the newly introduced genes at high levels, were selected and compared for the amount of antibody production and the survival rate. In fed-batch culture in 50-mL shaker flasks under the condition of $2\times10^5$ cells/mL in an initial stage, the AE1/CSAD co-expressing strains (nine strains) showed significantly greater amounts of anti-glypican-3 antibody production (t-test $P<0.05$, FIG. 9) and significantly higher survival rates (t-test $P<0.01$, FIG. 10) than the control AE1/pPur co-expressing strain (eight strains) on day 10 at the late stage of the shake culture. Among the three kinds of co-expressing strains, AE1/ALT1 co-expressing strains (10 strains) produced the largest amount of an anti-glypican-3 antibody, which was significantly greater than that produced by the control AE1/pPur co-expressing strains (eight strains) on day 8 of the shaker fed-batch culture (t-test $P<0.01$, FIG. 11). Subsequently, AA53, which produced the largest amount of an antibody (1497 mg/L/8 days) and expressed ALT1 mRNA at the highest level among the AE1/ALT1 co-expressing strains (10 strains) in the study using the shaker fed-batch culture, was subjected to fed-batch culture in a 1-L jar ($10\times10^5$ cells/mL in an initial stage). Then, the amount of an antibody produced by AA53 on day 7 of the culture was found to be 1.9 g/L/7 days, revealing that AA53 was capable of high-yield antibody production in short-term culture (FIG. 12). Considering that TA41, which was a TauT/ALT1 co-expressing strain that produced 5.3 g/L of an antibody on day 21 of the culture (see Example 2 in WO2009/020144), produced 1.5 g/L of an antibody on day 7 of the culture, AA53 has a potential to produce a greater amount of an antibody in a short time than does TA41, and hence, AA53 is considered to be suitable for practical production.

The above results show that cells capable of high-yield antibody production can be obtained by strongly expressing an anion exchanger (AE1) artificially, and by strongly expressing AE1 and CSAD or ALT1 simultaneously.

All publications, patent and patent applications cited herein are incorporated herein by reference in their entirety.

Industrial Applicability

The present invention is applicable to production of proteins.

Sequence Listing Free Text

<SEQ ID NO: 1>
SEQ ID NO: 1 shows the nucleotide sequence of a gene encoding human AE1 (GenBank M27819).

<SEQ ID NO: 2>
SEQ ID NO: 2 shows the amino acid sequence of human AE1 (UniProtKB/Swiss-Prot P02730).

<SEQ ID NO: 3>
SEQ ID NO: 3 shows the nucleotide sequence of a gene encoding human ALT1 (KEGG/ENZYME: 2.6.1.2/*Homo sapiens* (human): 2875).

<SEQ ID NO: 4>
SEQ ID NO: 4 shows the amino acid sequence of human ALT1 (KEGG/ENZYME: 2.6.1.2/*Homo sapiens* (human): 2875).

<SEQ ID NO: 5>
SEQ ID NO: 5 shows a Kozak sequence.

<SEQ ID NO: 6>
SEQ ID NO: 6 shows a secretion signal peptide sequence.

Citation List

Patent Document 1: Japanese Examined Patent Publication No. 6-30588

The invention claimed is:

1. A method for producing a cell capable of high-yield production of a desired polypeptide, comprising culturing a cell into which a bicarbonate transporter gene has been artificially transferred and into which DNA encoding the desired polypeptide has been introduced, in the presence of a high concentration of methotrexate and selecting a cell capable of high-yield production of the desired polypeptide from among surviving cells.

2. The method according to claim 1, wherein DNA encoding dihydrofolate reductase is also introduced into the cell into which a bicarbonate transporter gene has been artificially transferred and into which DNA encoding the desired polypeptide has been introduced.

3. The method according to claim 2, wherein the cell into which a bicarbonate transporter gene has been artificially transferred and into which DNA encoding the desired polypcptide has been introduced is a cell that is co-transformed with one molecule containing DNA encoding the desired polypcptide and DNA encoding dihydrofolate reductase.

4. The method according to claim 3, wherein the molecule containing DNA encoding the desired polypeptide and DNA encoding dihydrofolate reductase is a vector.

5. The method according claim 1, wherein the cell into which a bicarbonate transporter gene has been artificially transferred also strongly expresses alanine aminotransferase.

6. A cell produced by a method according to claim 1.

7. A method for producing a desired polypeptide comprising culturing the cell according to claim 6.

8. The method according to claim 7, wherein the desired polypeptide is an antibody.

9. A pharmaceutical product containing a polypeptide produced by the method according to claim 7.

10. A method for enhancing the amount of polypeptide production by a cell into which a bicarbonate transporter gene has been artificially transferred and into which DNA encoding a desired polypeptide has been introduced, the method comprising treating the cell with a high concentration of methotrexate.

11. The method according to claim 10. wherein DNA encoding dihydrofolate reductase is also introduced into the cell into which a bicarbonate transporter gene has been artificially transferred and into which DNA encoding the desired polypeptide has been introduced.

12. The method according to claim 11, wherein the cell into which a bicarbonate transporter gene has been artificially transferred and into which DNA encoding the desired polypeptide has been introduced is a cell that is co-transformed with one molecule containing DNA encoding the desired polypeptide and DNA encoding dihydrofolate reductase.

13. The method according to claim 10, wherein the strongly cell into which a bicarbonate transporter gene has been artificially transferred also strongly expresses alanine aminotransferase.

14. A method for preparing a cell with a high survival rate in a culture comprising methotrexate at a high concentration, comprising artificially transferring a bicarbonate transporter bene into the cell.

15. A method for producing a cell capable of high-yield production of a desired polypeptide comprising culturing a cell into which a bicarbonate transporter gene has been artificially transferred and into which DNA encoding the desired polypeptide has been introduced in the presence of methotrexate and selecting a cell capable of high-yield production of the desired polypeptide from among surviving cells.

16. A method for enhancing the amount of polypeptide produced by a cell into which a bicarbonate transporter gene has been artificially transferred and into which DNA encoding a desired polypeptide has been introduced, the method comprising treating the cell with methotrexate.

* * * * *

SEQUENCE LISTING

<160> NUMBER OF SEQ ID NOS: 6

<210> SEQ ID NO 1
<211> LENGTH: 2736
<212> TYPE: DNA
<213> ORGANISM: Homo sapiens

<400> SEQUENCE: 1

```
atggaggagc tgcaggatga ttatgaagac atgatggagg agaatctgga gcaggaggaa      60
tatgaagacc cagacatccc cgagtcccag atggaggagc cggcagctca cgacaccgag     120
gcaacagcca cagactacca caccacatca cacccgggta cccacaaggt ctatgtggag     180
ctgcaggagc tggtgatgga cgaaaagaac caggagctga gatggatgga ggcggcgcgc     240
tgggtgcaac tggaggagaa cctgggggag aatggggcct ggggccgccc gcacctctct     300
cacctcacct tctggagcct cctagagctg cgtagagtct tcaccaaggg tactgttctc     360
ctagacctgc aagagacctc cctggctgga gtggccaacc aactgctaga caggtttatc     420
tttgaagacc agatccggcc tcaggaccga gaggagctgc ccgggccct gctgcttaaa     480
cacagccacg ctggagagct ggaggccctg ggggtgtga agcctgcagt cctgacacgc     540
tctgggatc cttcacagcc tctgctcccc caacactcct cactggagac acagctcttc     600
tgtgagcagg gagatggggg cacagaaggg cactcaccat ctggaattct ggaaaagatt     660
cccccggatt cagaggccac gttggtgcta gtgggccgcg ccgacttcct ggagcagccg     720
gtgctgggct tcgtgaggct gcaggaggca gcggagctgg aggcggtgga gctgccggtg     780
cctatacgct tcctctttgt gttgctggga cctgaggccc ccacatcga ttacacccag     840
cttgccggg ctgctgccac cctcatgtca gagaggtgt tccgcataga tgcctacatg     900
gctcagagcc gagggagct gctgcactcc ctagagggct tcctggactg cagcctagtg     960
ctgcctccca ccgatgcccc ctccgagcag gcactgctca gtctggtgcc tgtgcagagg    1020
gagctacttc gaaggcgcta tcagtccagc cctgccaagc cagactccag cttctacaag    1080
ggcctagact taaatggggg cccagatgac cctctgcagc agacaggcca gctcttcggg    1140
ggcctggtgc gtgatatccg gcgccgctac ccctattacc tgagtgacat cacagatgca    1200
ttcagccccc aggtcctggc tgccgtcatc ttcatctact tgctgcact gtcacccgcc    1260
atcaccttcg gcggcctcct gggagaaaag acccggaacc agatgggagt gtcggagctg    1320
ctgatctcca ctgcagtgca gggcattctc ttcgccctgc tgggggctca gccctgctt    1380
gtggtcggct tctcaggacc cctgctggtg tttgaggaag ccttcttctc gttctgcgag    1440
accaacggtc tagagtacat cgtgggccgc gtgtggatcg gcttctggct catcctgctg    1500
gtggtgttgg tggtggcctt cgagggtagc ttcctggtcc gcttcatctc ccgctatacc    1560
caggagatct tctccttcct catttccctc atcttcatct atgagacttt ctccaagctg    1620
atcaagatct tccaggacca cccactacag aagacttata actacaacgt gttgatggtg    1680
cccaaacctc agggccccct gcccaacaca gccctcctct cccttgtgct catggccggt    1740
accttcttct ttgccatgat gctgcgcaag ttcaagaaca gctcctattt ccctggcaag    1800
ctgcgtcggg tcatcgggga cttcggggtc cccatctcca tcctgatcat ggtcctggtg    1860
gatttcttca ttcaggatac ctacacccag aaactctcgg tgcctgatgg cttcaaggtg    1920
tccaactcct cagcccgggg ctgggtcatc cacccactgg gcttgcgttc gagtttccc    1980
atctggatga tgtttgcctc cgccctgcct gctctgctgg tcttcatcct catattcctg    2040
gagtctcaga tcaccacgct gattgtcagc aaacctgagc gcaagatggt caagggctcc    2100
ggcttccacc tggacctgct gctggtagta ggcatgggtg gggtggccgc cctctttggg    2160
atgccctggc tcagtgccac caccgtgcgt tccgtcaccc atgccaacgc cctcactgtc    2220
atgggcaaag ccagcacccc aggggctgca gcccagatcc aggaggtcaa agagcagcgg    2280
atcagtggac tcctggtcgc tgtgcttgtg ggcctgtcca tcctcatgga gccatcctg    2340
```

```
tcccgcatcc ccctggctgt actgtttggc atcttcctct acatgggggt cacgtcgctc    2400
agcggcatcc agctctttga ccgcatcttg cttctgttca agccacccaa gtatcaccca    2460
gatgtgccct acgtcaagcg ggtgaagacc tggcgcatgc acttattcac gggcatccag    2520
atcatctgcc tggcagtgct gtgggtggtg aagtccacgc cggcctccct ggccctgccc    2580
ttcgtcctca tcctcactgt gccgctgcgg cgcgtcctgc tgccgctcat cttcaggaac    2640
gtggagcttc agtgtctgga tgctgatgat gccaaggcaa cctttgatga ggaggaaggt    2700
cgggatgaat acgacgaagt ggccatgcct gtgtga                             2736
```

<210> SEQ ID NO 2
<211> LENGTH: 911
<212> TYPE: PRT
<213> ORGANISM: Homo sapiens

<400> SEQUENCE: 2

```
Met Glu Glu Leu Gln Asp Asp Tyr Glu Asp Met Met Glu Glu Asn Leu
1               5                   10                  15

Glu Gln Glu Glu Tyr Glu Asp Pro Asp Ile Pro Glu Ser Gln Met Glu
            20                  25                  30

Glu Pro Ala Ala His Asp Thr Glu Ala Thr Ala Thr Asp Tyr His Thr
        35                  40                  45

Thr Ser His Pro Gly Thr His Lys Val Tyr Val Leu Gln Glu Leu
    50                  55                  60

Val Met Asp Glu Lys Asn Gln Glu Leu Arg Trp Met Glu Ala Ala Arg
65                  70                  75                  80

Trp Val Gln Leu Glu Glu Asn Leu Gly Glu Asn Gly Ala Trp Gly Arg
                85                  90                  95

Pro His Leu Ser His Leu Thr Phe Trp Ser Leu Leu Glu Leu Arg Arg
            100                 105                 110

Val Phe Thr Lys Gly Thr Val Leu Leu Asp Leu Gln Glu Thr Ser Leu
        115                 120                 125

Ala Gly Val Ala Asn Gln Leu Leu Asp Arg Phe Ile Phe Glu Asp Gln
    130                 135                 140

Ile Arg Pro Gln Asp Arg Glu Glu Leu Leu Arg Ala Leu Leu Leu Lys
145                 150                 155                 160

His Ser His Ala Gly Glu Leu Glu Ala Leu Gly Gly Val Lys Pro Ala
                165                 170                 175

Val Leu Thr Arg Ser Gly Asp Pro Ser Gln Pro Leu Pro Gln His
            180                 185                 190

Ser Ser Leu Glu Thr Gln Leu Phe Cys Glu Gln Gly Asp Gly Gly Thr
        195                 200                 205

Glu Gly His Ser Pro Ser Gly Ile Leu Glu Lys Ile Pro Pro Asp Ser
    210                 215                 220

Glu Ala Thr Leu Val Leu Val Gly Arg Ala Asp Phe Leu Glu Gln Pro
225                 230                 235                 240

Val Leu Gly Phe Val Arg Leu Gln Glu Ala Ala Glu Leu Glu Ala Val
                245                 250                 255

Glu Leu Pro Val Pro Ile Arg Phe Leu Phe Val Leu Leu Gly Pro Glu
            260                 265                 270

Ala Pro His Ile Asp Tyr Thr Gln Leu Gly Arg Ala Ala Ala Thr Leu
        275                 280                 285

Met Ser Glu Arg Val Phe Arg Ile Asp Ala Tyr Met Ala Gln Ser Arg
    290                 295                 300
```

```
Gly Glu Leu Leu His Ser Leu Glu Gly Phe Leu Asp Cys Ser Leu Val
305                 310                 315                 320

Leu Pro Pro Thr Asp Ala Pro Ser Glu Gln Ala Leu Leu Ser Leu Val
            325                 330                 335

Pro Val Gln Arg Glu Leu Leu Arg Arg Arg Tyr Gln Ser Ser Pro Ala
            340                 345                 350

Lys Pro Asp Ser Ser Phe Tyr Lys Gly Leu Asp Leu Asn Gly Gly Pro
            355                 360                 365

Asp Asp Pro Leu Gln Gln Thr Gly Gln Leu Phe Gly Gly Leu Val Arg
370                 375                 380

Asp Ile Arg Arg Tyr Pro Tyr Tyr Leu Ser Asp Ile Thr Asp Ala
385                 390                 395                 400

Phe Ser Pro Gln Val Leu Ala Ala Val Ile Phe Ile Tyr Phe Ala Ala
            405                 410                 415

Leu Ser Pro Ala Ile Thr Phe Gly Gly Leu Leu Gly Glu Lys Thr Arg
            420                 425                 430

Asn Gln Met Gly Val Ser Glu Leu Leu Ile Ser Thr Ala Val Gln Gly
            435                 440                 445

Ile Leu Phe Ala Leu Leu Gly Ala Gln Pro Leu Leu Val Val Gly Phe
450                 455                 460

Ser Gly Pro Leu Leu Val Phe Glu Glu Ala Phe Phe Ser Phe Cys Glu
465                 470                 475                 480

Thr Asn Gly Leu Glu Tyr Ile Val Gly Arg Val Trp Ile Gly Phe Trp
            485                 490                 495

Leu Ile Leu Leu Val Val Leu Val Val Ala Phe Glu Gly Ser Phe Leu
            500                 505                 510

Val Arg Phe Ile Ser Arg Tyr Thr Gln Glu Ile Phe Ser Phe Leu Ile
            515                 520                 525

Ser Leu Ile Phe Ile Tyr Glu Thr Phe Ser Lys Leu Ile Lys Ile Phe
            530                 535                 540

Gln Asp His Pro Leu Gln Lys Thr Tyr Asn Tyr Asn Val Leu Met Val
545                 550                 555                 560

Pro Lys Pro Gln Gly Pro Leu Pro Asn Thr Ala Leu Leu Ser Leu Val
            565                 570                 575

Leu Met Ala Gly Thr Phe Phe Phe Ala Met Met Leu Arg Lys Phe Lys
            580                 585                 590

Asn Ser Ser Tyr Phe Pro Gly Lys Leu Arg Arg Val Ile Gly Asp Phe
            595                 600                 605

Gly Val Pro Ile Ser Ile Leu Ile Met Val Leu Val Asp Phe Phe Ile
            610                 615                 620

Gln Asp Thr Tyr Thr Gln Lys Leu Ser Val Pro Asp Gly Phe Lys Val
625                 630                 635                 640

Ser Asn Ser Ser Ala Arg Gly Trp Val Ile His Pro Leu Gly Leu Arg
            645                 650                 655

Ser Glu Phe Pro Ile Trp Met Met Phe Ala Ser Ala Leu Pro Ala Leu
            660                 665                 670

Leu Val Phe Ile Leu Ile Phe Leu Glu Ser Gln Ile Thr Thr Leu Ile
            675                 680                 685

Val Ser Lys Pro Glu Arg Lys Met Val Lys Gly Ser Gly Phe His Leu
            690                 695                 700

Asp Leu Leu Leu Val Val Gly Met Gly Gly Val Ala Ala Leu Phe Gly
705                 710                 715                 720

Met Pro Trp Leu Ser Ala Thr Thr Val Arg Ser Val Thr His Ala Asn
            725                 730                 735
```

```
Ala Leu Thr Val Met Gly Lys Ala Ser Thr Pro Gly Ala Ala Gln
            740                 745                 750

Ile Gln Glu Val Lys Glu Gln Arg Ile Ser Gly Leu Leu Ala Val
        755                 760                 765

Leu Val Gly Leu Ser Ile Leu Met Glu Pro Ile Leu Ser Arg Ile Pro
770                 775                 780

Leu Ala Val Leu Phe Gly Ile Phe Leu Tyr Met Gly Val Thr Ser Leu
785                 790                 795                 800

Ser Gly Ile Gln Leu Phe Asp Arg Ile Leu Leu Phe Lys Pro Pro
                805                 810                 815

Lys Tyr His Pro Asp Val Pro Tyr Val Lys Arg Val Lys Thr Trp Arg
                820                 825                 830

Met His Leu Phe Thr Gly Ile Gln Ile Ile Cys Leu Ala Val Leu Trp
            835                 840                 845

Val Val Lys Ser Thr Pro Ala Ser Leu Ala Leu Pro Phe Val Leu Ile
850                 855                 860

Leu Thr Val Pro Leu Arg Arg Val Leu Leu Pro Leu Ile Phe Arg Asn
865                 870                 875                 880

Val Glu Leu Gln Cys Leu Asp Ala Asp Asp Ala Lys Ala Thr Phe Asp
                885                 890                 895

Glu Glu Glu Gly Arg Asp Glu Tyr Asp Glu Val Ala Met Pro Val
                900                 905                 910

<210> SEQ ID NO 3
<211> LENGTH: 1491
<212> TYPE: DNA
<213> ORGANISM: Homo sapiens

<400> SEQUENCE: 3
atggcctcga gcacaggtga ccggagccag gcggtgaggc atggactgag ggcgaaggtg      60
ctgacgctgg acggcatgaa cccgcgtgtg cggagagtgg agtacgcagt gcgtggcccc     120
atagtgcagc gagccttgga gctggagcag gagctgcgcc agggtgtgaa gaagcctttc     180
accgaggtca tccgtgccaa catcggggac gcacaggcta tggggcagag gcccatcacc     240
ttcctgcgcc aggtcttggc cctctgtgtt aaccctgatc ttctgagcag ccccaacttc     300
cctgacgatg ccaagaaaag gcggagcgc atcttgcagg cgtgtggggg ccacagtctg     360
ggggcctaca gcgtcagctc cggcatccag ctgatccggg aggacgtggc gcggtacatt     420
gagaggcgtg acgaggcat ccctgcggac cccaacaacg tcttcctgtc cacaggggcc     480
agcgatgcca tcgtgacggt gctgaagctg ctggtggccg gcgagggcca cacgcacg     540 ggtgtgctca tccccatccc ccagtaccca ctctactcgg ccacgctggc agagctgggc     600
gcagtgcagg tggattacta cctggacgag gagcgtgcct gggcgctgga cgtggccgag     660
cttcaccgtg cactgggcca ggcgcgtgac cactgccgcc ctcgtgcgct ctgtgtcatc     720
aaccctggca ccccaccgg gcaggtgcag acccgcgagt gcatcgaggc cgtgatccgc     780
ttcgccttcg aagagcggct ctttctgctg cggacgagg tgtaccagga caacgtgtac     840
gccgcgggtt cgcagttcca ctcattcaag aaggtgctca tggagatggg gccgccctac     900
gccgggcagc aggagcttgc ctccttccac tccacctcca agggctacat gggcgagtgc     960
gggttccgcg cggctatgt ggaggtggtg aacatggacg ctgcagtgca gcagcagatg    1020
ctgaagctga tgagtgtgcg gctgtgcccg ccggtgccag acaggccct gctggacctg    1080 gtggtcagcc cgcccgcgcc caccgacccc tcctttgcgc agttccaggc tgagaagcag    1140
```

-continued

```
gcagtgctgg cagagctggc ggccaaggcc aagctcaccg agcaggtctt caatgaggct      1200
cctggcatca gctgcaaccc agtgcagggc gccatgtact ccttcccgcg cgtgcagctg      1260
cccccgcggg cggtggagcg cgctcaggag ctgggcctgg cccccgatat gttcttctgc      1320
ctgcgcctcc tggaggagac cggcatctgc gtggtgccag ggagcggctt tgggcagcgg      1380
gaaggcacct accacttccg gatgaccatt ctgcccccct tggagaaact gcggctgctg      1440
ctggagaagc tgagcaggtt ccatgccaag ttcaccctcg agtactcctg a               1491
```

<210> SEQ ID NO 4
<211> LENGTH: 496
<212> TYPE: PRT
<213> ORGANISM: Homo sapiens

<400> SEQUENCE: 4

```
Met Ala Ser Ser Thr Gly Asp Arg Ser Gln Ala Val Arg His Gly Leu
1               5                   10                  15

Arg Ala Lys Val Leu Thr Leu Asp Gly Met Asn Pro Arg Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Leu Arg Gln Val Leu Ala Leu Cys Val Asn Pro Asp Leu Leu Ser
                85                  90                  95

Ser Pro Asn Phe Pro Asp Asp Ala Lys Lys Arg Ala Glu Arg Ile Leu
            100                 105                 110

Gln Ala Cys Gly Gly His Ser Leu Gly Ala Tyr Ser Val Ser Ser Gly
        115                 120                 125

Ile Gln Leu Ile Arg Glu Asp Val Ala Arg Tyr Ile Glu Arg Arg Asp
    130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
                165                 170                 175

His Thr Arg Thr Gly Val Leu Ile Pro Ile Pro Gln Tyr Pro Leu Tyr
            180                 185                 190

Ser Ala Thr Leu Ala Glu Leu Gly Ala Val Gln Val Asp Tyr Tyr Leu
        195                 200                 205

Asp Glu Glu Arg Ala Trp Ala Leu Asp Val Ala Glu Leu His Arg Ala
    210                 215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
            260                 265                 270

Glu Val Tyr Gln Asp Asn Val Tyr Ala Ala Gly Ser Gln Phe His Ser
        275                 280                 285

Phe Lys Lys Val Leu Met Glu Met Gly Pro Pro Tyr Ala Gly Gln Gln
    290                 295                 300

Glu Leu Ala Ser Phe His Ser Thr Ser Lys Gly Tyr Met Gly Glu Cys
305                 310                 315                 320
```

```
Gly Phe Arg Gly Gly Tyr Val Glu Val Val Asn Met Asp Ala Ala Val
                325                 330                 335

Gln Gln Gln Met Leu Lys Leu Met Ser Val Arg Leu Cys Pro Pro Val
            340                 345                 350

Pro Gly Gln Ala Leu Leu Asp Leu Val Val Ser Pro Pro Ala Pro Thr
        355                 360                 365

Asp Pro Ser Phe Ala Gln Phe Gln Ala Glu Lys Gln Ala Val Leu Ala
    370                 375                 380

Glu Leu Ala Ala Lys Ala Lys Leu Thr Glu Gln Val Phe Asn Glu Ala
385                 390                 395                 400

Pro Gly Ile Ser Cys Asn Pro Val Gln Gly Ala Met Tyr Ser Phe Pro
                405                 410                 415

Arg Val Gln Leu Pro Pro Arg Ala Val Glu Arg Ala Gln Glu Leu Gly
            420                 425                 430

Leu Ala Pro Asp Met Phe Phe Cys Leu Arg Leu Leu Glu Glu Thr Gly
        435                 440                 445

Ile Cys Val Val Pro Gly Ser Gly Phe Gly Gln Arg Glu Gly Thr Tyr
    450                 455                 460

His Phe Arg Met Thr Ile Leu Pro Pro Leu Glu Lys Leu Arg Leu Leu
465                 470                 475                 480

Leu Glu Lys Leu Ser Arg Phe His Ala Lys Phe Thr Leu Glu Tyr Ser
                485                 490                 495

<210> SEQ ID NO 5
<211> LENGTH: 10
<212> TYPE: RNA
<213> ORGANISM: Artificial
<220> FEATURE:
<223> OTHER INFORMATION: Kozal sequence

<400> SEQUENCE: 5 gccrccaugg                                                                10

<210> SEQ ID NO 6
<211> LENGTH: 19
<212> TYPE: PRT
<213> ORGANISM: Artificial
<220> FEATURE:
<223> OTHER INFORMATION: Secretion signal sequence

<400> SEQUENCE: 6

Met Gly Trp Ser Cys Ile Ile Leu Phe Leu Val Ala Thr Ala Thr Gly
1               5                   10                  15

Val His Ser
```